United States Patent
Freeman et al.

(10) Patent No.: US 11,622,726 B2
(45) Date of Patent: Apr. 11, 2023

(54) USE OF MUSCLE OXYGEN SATURATION AND PH IN CLINICAL DECISION SUPPORT

(71) Applicant: ZOLL MEDICAL CORPORATION, Chelmsford, MA (US)

(72) Inventors: Gary A. Freeman, Newton Center, MA (US); Annemarie Elizabeth Silver, Bedford, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 683 days.

(21) Appl. No.: 14/227,785

(22) Filed: Mar. 27, 2014

(65) Prior Publication Data

US 2014/0296675 A1    Oct. 2, 2014

Related U.S. Application Data

(60) Provisional application No. 61/805,857, filed on Mar. 27, 2013.

(51) Int. Cl.
*A61B 5/00* (2006.01)
*A61B 5/145* (2006.01)
(Continued)

(52) U.S. Cl.
CPC .......... *A61B 5/7264* (2013.01); *A61B 5/0836* (2013.01); *A61B 5/1468* (2013.01);
(Continued)

(58) Field of Classification Search
CPC .............. A61B 5/0836; A61B 5/14539; A61B 5/14542; A61B 5/4836; A61B 5/742
See application file for complete search history.

(56) References Cited

U.S. PATENT DOCUMENTS

| 4,928,674 A * | 5/1990 | Halperin | A61H 9/0078 600/495 |
|---|---|---|---|
| 2002/0091687 A1* | 7/2002 | Eglington | G16H 50/20 707/999.005 |

(Continued)

OTHER PUBLICATIONS

Soller et al, Noninvasively determined muscle oxygen saturation is an early indicator of central hypovolemia in humans, 2008, J Appl Physiol, 104(2): 475-481.*

(Continued)

*Primary Examiner* — Jay B Shah
(74) *Attorney, Agent, or Firm* — Fish & Richardson P.C.

(57) ABSTRACT

Embodiments of the present invention include a system having at least one sensor configured to monitor a muscle oxygen saturation (SmO2) level of a patient who is undergoing cardiac arrest and to generate a signal representing SmO2 level; a user interface device; a processor communicably coupled to the user interface device, the processor configured to cause the user interface device to present an array of two or more possible nodes of a clinical decision support tree, wherein at least one of the nodes indicates cardiopulmonary resuscitation (CPR) treatment of the patient with no ventilation, and wherein at least another of the nodes indicates CPR treatment of the patient with active ventilation; determine which of the two or more possible nodes should be emphasized based on the SmO2 level; and update the array of the two or more possible nodes based on the determination.

22 Claims, 30 Drawing Sheets

(51) Int. Cl.
   A61B 5/083     (2006.01)
   A61B 5/1468    (2006.01)
   G16H 50/20     (2018.01)
   G16Z 99/00     (2019.01)
   H04M 1/04      (2006.01)
   A61H 31/00     (2006.01)
   G06K 9/00      (2022.01)
   A61N 1/39      (2006.01)
   H04M 1/72409   (2021.01)

(52) U.S. Cl.
   CPC ...... *A61B 5/14539* (2013.01); *A61B 5/14542* (2013.01); *A61B 5/4836* (2013.01); *A61B 5/742* (2013.01); *A61B 5/7475* (2013.01); *G16H 50/20* (2018.01); *G16Z 99/00* (2019.02); *A61H 31/005* (2013.01); *A61H 2201/501* (2013.01); *A61H 2201/5097* (2013.01); *A61H 2230/04* (2013.01); *A61H 2230/205* (2013.01); *A61H 2230/207* (2013.01); *A61H 2230/30* (2013.01); *A61H 2230/40* (2013.01); *A61H 2230/42* (2013.01); *A61N 1/3904* (2017.08); *G06K 9/00536* (2013.01); *H04M 1/04* (2013.01); *H04M 1/72409* (2021.01)

(56) References Cited

U.S. PATENT DOCUMENTS

| | | | | |
|---|---|---|---|---|
| 2004/0267324 A1* | 12/2004 | Geheb | ............... | A61B 5/11 607/5 |
| 2006/0223042 A1 | 10/2006 | Epler et al. | | |
| 2006/0229680 A1* | 10/2006 | Chapman | ............... | A61N 1/39 607/5 |
| 2008/0176199 A1* | 7/2008 | Stickney | ............... | G09B 23/288 434/265 |
| 2009/0275808 A1 | 11/2009 | DiMaio et al. | | |
| 2010/0082075 A1* | 4/2010 | Russell | ............... | A61N 1/3925 607/5 |
| 2010/0099999 A1* | 4/2010 | Hemnes | ............... | A61B 5/0836 600/532 |
| 2010/0174555 A1 | 7/2010 | Abraham-Fuchs et al. | | |
| 2011/0202100 A1* | 8/2011 | Tan | ............... | A61H 31/005 607/6 |
| 2011/0284004 A1* | 11/2011 | Silver | ............... | A61N 1/3925 128/205.13 |
| 2012/0123223 A1 | 5/2012 | Freeman et al. | | |
| 2012/0123224 A1* | 5/2012 | Packer | ............... | G06F 19/3418 600/301 |

OTHER PUBLICATIONS

American Heart Association, ACLS Algorithms, 2010, Web, Retrieved from: http://www.uwhealth.org/files/uwhealth/docs/pdf4/EEC/acls_algorithms.pdf.*

Varma, Augmented reality: what does it mean for print?, 2011, Web, Retrieved from: http://graphicartsmag.com/articles/2011/06/augmented-reality-what-does-it-mean-for-print/.*

World Health Organization; Pulse Oximetry Training Manual; 2011 ; ISBN 978 92 4 150113 2 (Year: 2011).*

AED Algorithm Application Note; Koninklijke Philips Electronics N.V.; Published Sep. 2008, Edition 1, Printed in the USA 453564119761 (Year: 2008).*

CPR/AED for Professional Rescuers and Health Care Providers Handbook; American Red Cross; Stock No. 652168; ISBN: 978-1-58480-494-9 (Year: 2011).*

Sutin et al. The Electrocardiogram in Respiratory Distress Syndrome* The Praecordial P Wave as an Aid to Assessment; Arch. Dis. Childh., 1965, 40, 402. (Year: 1965).*

International Search Report and Written Opinion issued in PCT/US2014/032005 dated Nov. 3, 2014, 19 pages.

* cited by examiner

DIFFERENTIAL DIAGNOSIS OF ACUTE DYSPNEA IN ADULTS

CARDIAC: CONGESTIVE HEART FAILURE, CORONARY ARTERY DISEASE, ARRHYTHMIA, PERICARDITIS, ACUTE MYOCARDIAL INFARCTION, ANEMIA

PULMONARY: CHRONIC OBSTRUCTIVE PULMONARY DISEASE, ASTHMA, PNEUMONIA, PNEUMOTHORAX, PULMONARY EMBOLISM, PLEURAL EFFUSION, METASTATIC DISEASE, PULMONARY EDEMA, GASTROESOPHAGEAL REFLUX DISEASE WITH ASPIRATION, RESTRICTIVE LUNG DISEASE

PSYCHOGENIC: PANIC ATTACKS, HYPERVENTILATION, PAIN, ANXIETY

UPPER AIRWAY OBSTRUCTION: EPIGLOTTITIS, FOREIGN BODY, CROUP, EPSTEIN-BARR VIRUS

ENDOCRINE: METABOLIC ACIDOSIS, MEDICATIONS

CENTRAL: NEUROMUSCULAR DISORDERS, PAIN, ASPIRIN OVERDOSE

PEDIATRIC: BRONCHIOLITIS, CROUP, EPIGLOTTITIS, FOREIGN BODY ASPIRATION, MYOCARDITIS

FIG. 5

CLUES TO THE DIAGNOSIS OF DYSPNEA

| SYMPTOMS OR FEATURES IN THE HISTORY | POSSIBLE DIAGNOSIS |
|---|---|
| COUGH | ASTHMA, PNEUMONIA |
| SEVERE SORE THROAT | EPIGLOTTITIS |
| PLEURITIC CHEST PAIN | PERICARDITIS, PULMONARY EMBOLISM, PNEUMOTHORAX, PNEUMONIA |
| ORTHOPNEA, NOCTURNAL PAROXYSMAL DYSPNEA, EDEMA | CONGESTIVE HEART FAILURE |
| TOBACCO USE | CHRONIC OBSTRUCTIVE PULMONARY DISEASE, CONGESTIVE HEART FAILURE, PULMONARY EMBOLISM |
| INDIGESTION, DYSPHAGIA | GASTROESOPHAGEAL REFLUX DISEASE, ASPIRATION |
| BARKING COUGH | CROUP |

FIG. 6

PHYSICAL EXAMINATION FINDINGS IN THE DIAGNOSIS OF ACUTE DYSPNEA

| FINDINGS | POSSIBLE DIAGNOSIS |
|---|---|
| WHEEZING, PULSUS PARADOXUS, ACCESSORY MUSCLE USE | ACUTE ASTHMA, COPD EXACERBATION |
| WHEEZING, CLUBBING, BARREL CHEST, DECREASED BREATH SOUNDS | COPD EXACERBATION |
| FEVER, CRACKLES, INCREASED FREMITUS | PNEUMONIA |
| EDEMA, NECK VEIN DISTENSION, S3 OR S4, HEPATOJUGULAR REFLUX, MURMERS, RALES, HYPERTENSION, WHEEZING | CONGESTIVE HEART FAILURE, PULMONARY EDEMA |
| WHEEZING, FRICTION RUB, LOWER EXTREMITY SWELLING | PULMONARY EMBOLISM |
| ABSENT BREATH SOUNDS, HYPERRESONANCE | PNEUMOTHORAX |
| INSPIRATORY STRIDOR, RHONCHI, RETRACTIONS | CROUP |
| STRIDOR, DROOLING, FEVER | EPIGLOTTITIS |
| STRIDOR, WHEEZING, PERSISTENT PNEUMONIA | FOREIGN BODY ASPIRATION |
| WHEEZING, FLARING, INTERCOSTAL RETRACTIONS, APNEA | BRONCHIOLITIS |
| SIGHING | HYPERVENTILATION |

COPD = CHRONIC OBSTRUCTIVE PULMONARY DISEASE

FIG. 7

1. Complete a scene size-up and determine if the scene is safe to approach. If the scene becomes unsafe at any time, withdraw.

2. Determine and evaluate the mechanism of injury.

3. Determine the number of patients and initiate MCI plan as appropriate.

4. Complete initial assessment according to initial assessment protocol, with attention to airway, breathing and circulation 5. Consider the need for spinal stabilization.

6. Determine the patient's level of consciousness by use of the AVPU scale
    a. A – Alert
    b. V – Responsive to verbal stimuli
    c. P – Responsive to painful stimuli
    d. U – Unresponsive 7. Assess vital signs.

8. Identify patient priority and need for ALS care. Dispatch ALS, if necessary.

9. Complete an appropriate secondary physical exam (see below):
    a. Rapid Trauma Exam: for patients with multi-system trauma or single-system trauma with a high index of suspicion for serious mechanism of injury (MOI).
    b. Focused physical exam: for patients with isolated injuries resulting from low index of suspicion for serious MOI who have no critical criteria according to dispatching ALS protocols.

10. Treat all life threatening injuries as found.

11. Complete history of event and past medical history using SAMPLE & OPQRST.

12. Treat all non-life threatening injuries as time allows.

13. Transport immediately.

FIG. 13

| RAPID TRAUMA ASSESSMENT |
|---|
| DETERMINE MOI |
| ABC'S |
| CONSIDER C-SPINE STABILIZATION |
| HEAD<br>DCAP – BTLS<br>EARS: BLEEDING, DISCHARGE, BRUISING BEHIND EARS<br>PUPILS: EQUALITY & REACTIVITY, RACCOON EYES, IMPALED OBJECTS<br>MOUTH: RE-CHECK AIRWAY, DENTURES, LOOSE OR BROKEN TEETH<br>OCCLUSIONS, BLEEDING, VOMITUS, GAG REFLEX, ASSESS BREATHING |
| NECK<br>DCAP – BTLS<br>JVD, TRACHEAL DEVIATION<br>C-SPINE: DEFORMITY OR TENDERNESS<br>ACCESSORY MUSCLE USE IN RESPIRATION<br>BLUNT TRAUMA<br>BURNS |
| CHEST<br>DCAP – BTLS<br>EQUAL CHEST RISE AND FALL<br>OPEN WOUNDS, AIR LEAKS<br>BREATH SOUNDS |
| ABDOMEN<br>DCAP – BTLS<br>PULSATING MASS<br>PALPATE FOUR QUADRANTS<br>TENDERNESS & GUARDING<br>DISTENTION<br>SIGNS OF PREGNANCY |
| PELVIS<br>DCAP – BTLS<br>ASSESS FOR INSTABILITY<br>PRIAPISM<br>BLEEDING OR DISCHARGE |
| EXTREMITIES<br>DCAP – BTLS<br>PULSE, MOVEMENT AND SENSATION |
| POSTERIOR<br>DCAP – BTLS<br>LUNG SOUNDS<br>SKIN WOUNDS OR LESIONS |

FIG. 14

| FOCUSED PHYSICAL EXAM |
|---|
| DETERMINE MOI |
| ABC'S |
| CONSIDER C-SPINE STABILIZATION |
| ASSESS THE AFFECTED AREA |
| ASSESS THE AREAS "ABOVE" AND "BELOW" THE AFFECTED AREA |

FIG. 15

1. Follow initial assessment and trauma assessment protocols for general guidelines on patient care.

2. Control all major bleeding according to standard BLS techniques.

3. Administer oxygen according to oxygen administration protocol.

4. Make every effort to locate and transport the amputated appendage with the patient.

5. Wrap the appendage in moist sterile dressing and place it in a plastic bag. Use ice packs or ice to keep the appendage cool.

6. If possible, contact Medical Control prior to transport to ensure appropriateness of transport destination.

FIG. 16

1. Assess the patient according to initial assessment and trauma assessment protocols.

2. Monitor and maintain a patent airway. Ensure adequate respirations; assist respirations via BVM if indicated.

3. Evaluate for and attempt control of any major bleeding immediately. Use the following steps to control major bleeding:
   a. Apply direct pressure
   b. Elevate wound above the level of the heart, if feasible
   c. Apply pressure at the pulse point proximal to the wound
   d. Apply ice or cold pack
   e. Apply tourniquet 2 inches above the wound and tighten until bleeding stops. Mark the time of application around or on the tourniquet.

4. If a puncture wound is found in the chest, stomach or on the back, take the following steps:
   a. Immediately cover wound with a gloved hand
   b. Apply direct pressure
   c. Place occlusive dressing over wound
   d. Tape on three sides
   e. Evaluate for lung sounds around the site of the wound in the case of chest, upper back or upper abdominal wounds 5. Provide oxygen via NRB mask.

6. Evaluate all minor wounds after ensuring ABC's, completing assessment and treating all life threatening emergencies.

7. Bandage all wounds using proper BLS technique.

FIG. 17

1. Follow initial assessment and trauma assessment protocols for general patient care guidelines.

2. Pay close attention to airway and breathing considerations. Always be aware of possible compromise to airway and breathing caused by burns to the airway.

3. Provide oxygen via NRB at 15 lpm. Assist respirations with BVM as necessary.

4. Remove all clothing or restricting items on or around the burned area(s) if possible.

5. Determine the degree and extent of burns using the "rule of nines" when appropriate. Document findings in PCR.

6. Cover burns with sterile dressings.

7. Keep the patient warm and guard against hypothermia.

8. For significant burn injuries, contact Medical Control for decision regarding transport to trauma center or designated burn center.

FIG. 18

1. Follow Scene Safety protocol. Ensure that electrical source has been turned off by appropriately trained professionals and there is no danger to the rescuers while providing care. Stage away from the patient until such time as adequate scene safety can be assured.

2. Follow initial assessment and trauma assessment protocols for general patient care guidelines.

3. Ensure adequacy of airway, breathing and circulation.

4. Provide oxygen via NRB at 15 lpm or assist via BVM attached to supplemental oxygen at 15 lpm.

5. If pulse is absent:
   a. Begin CPR and attach AED.
   b. Defibrillate with AED as indicated.
   c. Ensure patent airway.

6. Consider transport options and need for assessment at trauma center or designated burn center.

FIG. 19

The following algorithm outlines requirements and indications for spinal immobilization. It is based on the algorithm published in the Pre-hospital Trauma Life Support curriculum.

Use this algorithm to evaluate and treat patients with known or suspected head trauma, spinal injuries, or mechanism of injury (MOI) which might indicate a need for immobilization.

Use clinical judgment in all cases. Where concerns exist, contact online medical control or immobilize and initiate transport. Whenever in doubt, err on the side of caution and maintain cervical spine immobilization.

FIG. 20

1. Assess patient according to initial assessment and trauma assessment protocols. Perform a rapid trauma exam.

2. Ensure airway and adequate respiratory effort. Provide oxygen via NRB at 15 lpm or assist respirations via BVM.

3. Assess circulatory status for adequate pulse and signs of hypoperfusion. Control hemorrhaging with pressure.

4. Establish C-spine precautions and prepare to immobilize patient.

5. Determine level of consciousness using AVPU scale and assess for altered mental status.

6. Treat all life-threatening injuries as soon as possible.

7. Obtain a complete set of vitals. Monitor and reassess vital signs continuously.

8. Initiate transport to the closest appropriate facility immediately. Notify receiving facility en route. For assistance with transport decisions, contact Medical Control.

FIG. 22

1. Assess patient according to initial assessment and trauma assessment protocols. Make a special effort to determine the amount of time that the patient was in the water or submerged under water.

2. Open and maintain patent airway. Be ready to suction water from airway as necessary.

3. Check for spontaneous respirations and for pulse

4. If spontaneous respirations are present, provide high concentrations of oxygen by NRB mask according to oxygen administration protocol. Assist via BVM if respiratory effort is inadequate.

5. If spontaneous pulse and respirations are absent, refer to cardiac arrest protocols. Initiate advanced airway procedures and defibrillate as necessary.

6. Transport immediately. Contact Medical Control for assistance in determining appropriate receiving facility.

FIG. 23

1. Assess patient according to initial assessment and trauma assessment protocols. Perform a rapid trauma exam.

2. Ensure patent airway and adequate respiratory effort. Provide oxygen via NRB at 15 lpm or assist via BVM if needed.

3. Assess circulatory status for adequate pulse and signs of hypoperfusion.

4. Establish C-spine precautions and prepare to immobilize patient.

5. Determine level of consciousness (by use of the AVPU scale) and assess for altered mental status.

6. Treat all life-threatening injuries as soon as possible.

7. Obtain a complete set of vitals. Monitor and reassess vital signs continuously.

8. Initiate transport to the closest appropriate facility immediately. Contact Medical Control for assistance in selecting most appropriate receiving facility.

9. Transport patient on the patient's left side, left lateral recumbent position, or raise the left side of the backboard at an angle greater than 15 degrees using towels, blankets, head-blocks, etc. (unless the patient is in cardiac arrest).

FIG. 24

1. Assess and treat patient according to initial assessment and trauma assessment protocols.

2. Immediately begin CPR and ventilate patient via BVM at 15 lpm.

3. Initiate basic airway management, per applicable protocols.

4. Transport immediately to the closest open trauma center. Notify receiving facility en route.

FIG. 25

USE OF MUSCLE OXYGEN SATURATION AND PH IN CLINICAL DECISION SUPPORT

CROSS-REFERENCE TO RELATED APPLICATIONS

This application claims the benefit of U.S. Provisional Patent Application Ser. No. 61/805,857, filed on Mar. 27, 2013, which is incorporated by reference herein in its entirety for all purposes.

TECHNICAL FIELD

Embodiments of the present invention relate generally to tools for facilitating acute care treatment, and more specifically to systems and methods for clinical decision support and differential diagnosis.

BACKGROUND

In the pre-hospital and acute care treatment setting, medical responders often have difficulties in accurately determining the proper diagnosis of a particular patient. Even well-trained physicians often have difficulty under emergency conditions in which split second decisions are required with limited information. Computer-automated diagnosis was developed to improve the accuracy, effectiveness, and reliability of both field and hospital patient treatment.

Automated differential diagnosis utilizes computer inference algorithms such as Bayesian algorithms, neural networks, or genetic algorithms. According to a Wikipedia posting:

The Bayesian network is a knowledge-based graphical representation that shows a set of variables and their probabilistic relationships between diseases and symptoms. They are based on conditional probabilities, the probability of an event given the occurrence of another event, such as the interpretation of diagnostic tests. Bayes' rule helps us compute the probability of an event with the help of some more readily information and it consistently processes options as new evidence is presented. In the context of CDSS [(clinical decision support system)], the Bayesian network can be used to compute the probabilities of the presence of the possible diseases given their symptoms. Some of the advantages of Bayesian Network include the knowledge and conclusions of experts in the form of probabilities, assistance in decision making as new information is available and are based on unbiased probabilities that are applicable to many models. Some of the disadvantages of Bayesian Network include the difficulty to get the probability knowledge for possible diagnosis and not being practical for large complex systems given multiple symptoms. The Bayesian calculations on multiple simultaneous symptoms could be overwhelming for users. Example of a Bayesian network in the CDSS context is the Iliad system which makes use of Bayesian reasoning to calculate posterior probabilities of possible diagnoses depending on the symptoms provided. The system now covers about 1500 diagnoses based on thousands of findings. Another example is the DXplain system that uses a modified form of the Bayesian logic. This CDSS produces a list of ranked diagnoses associated with the symptoms.

Artificial Neural Networks (ANN) is a nonknowledge-based adaptive CDSS that uses a form of artificial intelligence, also known as machine learning, that allows the systems to learn from past experiences/examples and recognizes patterns in clinical information. It consists of nodes called neurodes and weighted connections that transmit signals between the neurodes in a unidirectional fashion. An ANN consists of 3 main layers: Input (data receiver or findings), Output (communicates results or possible diseases) and Hidden (processes data). The system becomes more efficient with known results for large amounts of data. The advantages of ANN include the elimination of needing to program the systems and providing input from experts. The ANN CDSS can process incomplete data by making educated guesses about missing data and improves with every use due to its adaptive system learning. Additionally, ANN systems do not require large databases to store outcome data with its associated probabilities. Some of the disadvantages are that the training process may be time consuming leading users to not make use of the systems effectively. The ANN systems derive their own formulas for weighting and combining data based on the statistical recognition patterns over time which may be difficult to interpret and doubt the system's reliability. Examples include the diagnosis of appendicitis, back pain, myocardial infarction, psychiatric emergencies and skin disorders. The ANN's diagnostic predictions of pulmonary embolisms were in some cases even better than physician's predictions. Additionally, ANN based applications have been useful in the analysis of ECG (a.k.a. EKG) waveforms.

A Genetic Algorithm (GA) is a nonknowledge-based method developed in the 1940s at the Massachusetts Institute of Technology based on Darwin's evolutionary theories that dealt with the survival of the fittest. These algorithms rearrange to form different re-combinations that are better than the previous solutions. Similar to neural networks, the genetic algorithms derive their information from patient data. An advantage of genetic algorithms is these systems go through an iterative process to produce an optimal solution. The fitness function determines the good solutions and the solutions that can be eliminated. A disadvantage is the lack of transparency in the reasoning involved for the decision support systems making it undesirable for physicians. The main challenge in using genetic algorithms is in defining the fitness criteria. In order to use a genetic algorithm, there must be many components such as multiple drugs, symptoms, treatment therapy and so on available in order to solve a problem. Genetic algorithms have proved to be useful in the diagnosis of female urinary incontinence.

Despite the fact that automated differential diagnosis systems have been developed and attempted to be implemented for more than 35 years now, they have not achieved any acceptance in the emergency medical setting for acute care treatment (ACT). In large part, this failure is due to the conditions under which emergency care of acute conditions are practiced. In those situations, such as the treatment of trauma, cardiac arrest or respiratory arrest, speed of decision-making is critical and caregivers already must split their time and attention between the patient and the physiological monitors and defibrillators. In such situations, automated differential diagnosis (ADD) tools are often viewed as interfering with the caregiving process and as a delay to treatment of the patient. Given that every minute can result in a 10% drop in survival rate, such as is the case for cardiac arrest, it is not surprising that ADD tools are ignored by the very people that they were designed to assist.

It has also been found that much of the patient's medical history is inaccessible by the caregiver at the time of the acute medical condition because patients are often treated in the prehospital setting where family members are often not present at the time of the injury.

SUMMARY

A medical system according to some embodiments of the present invention includes at least one sensor configured to monitor a muscle oxygen saturation (SmO2) level, end tidal carbon dioxide (ETCO2) level, pH level, and/or hematocrit level of a patient who is undergoing cardiac arrest and to generate a signal representing the SmO2 level, end tidal carbon dioxide (ETCO2) level, pH, and/or hematocrit level. A separate sensor may be used for each of SmO2, ETCO2, pH, and hematocrit levels; alternatively, the same sensor may sense or determine two or more such values, according to embodiments of the present invention. A user interface device, a processor communicably coupled to the user interface device, the processor configured to: cause the user interface device to present an array of two or more possible nodes of a clinical decision support tree, wherein at least one of the two or more possible nodes indicates cardiopulmonary resuscitation (CPR) treatment of the patient with no ventilation, and wherein at least another of the two or more possible nodes indicates CPR treatment of the patient with active ventilation, determine which of the two or more possible nodes should be emphasized based on the SmO2, ETCO2, pH level, and/or hematocrit level and update the array of the two or more possible nodes based on the determination.

A medical system according to embodiments of the present invention includes at least one sensor configured to monitor a muscle oxygen saturation (SmO2) level, end tidal carbon dioxide (ETCO2) level, and/or pH level of a patient who is undergoing cardiac arrest and to generate a signal representing the SmO2, ETCO2, and/or pH level; a user interface device; a processor communicably coupled to the user interface device, the processor configured to: compare the SmO2 level and/or ETCO2 level and/or pH level over time with a predetermined threshold level; and indicate via the user interface device whether further cardiopulmonary resuscitation attempts are likely to be successful, based on the SmO2, ETCO2, and/or pH level.

A medical system according to embodiments of the present invention includes at least one sensor configured to monitor a muscle oxygen saturation (SmO2) level of a patient who is undergoing cardiac arrest and to generate a signal representing the SmO2 level; a user interface device; a processor communicably coupled to the user interface device, the processor configured to: cause the user interface device to present an array of two or more possible nodes of a clinical decision support tree, wherein at least one of the two or more possible nodes indicates cardiopulmonary resuscitation (CPR) treatment of the patient with no ventilation, and wherein at least another of the two or more possible nodes indicates CPR treatment of the patient with active ventilation; determine which of the two or more possible nodes should be emphasized based on the SmO2 level; and update the array of the two or more possible nodes based on the determination.

A medical system as described in one or more of the above paragraphs, wherein the processor is further configured to: receive a pH level of a muscle of the patient, and determine which of the two or more possible nodes should be emphasized based on the SMO2 level and the pH level.

A medical system as described in one or more of the above paragraphs, wherein the processor is further configured to update the array by visually emphasizing the one of the two or more possible nodes that should be emphasized as compared to an other of the two or more possible nodes.

A medical system as described in one or more of the above paragraphs, wherein visually emphasizing the one of the two or more possible nodes includes changing a color of the one of the two or more possible nodes.

A medical system as described in one or more of the above paragraphs, wherein visually emphasizing the one of the two or more possible nodes includes changing a size of the one of the two or more possible nodes.

A medical system as described in one or more of the above paragraphs, wherein visually emphasizing the one of the two or more possible nodes includes changing a shape of the one of the two or more possible nodes.

A method for clinical decision support in a cardiac arrest medical response according to embodiments of the present invention includes monitoring a muscle oxygen saturation (SmO2) level of a patient who is undergoing cardiac arrest; generating a signal representing the SmO2 level; displaying on a user interface device an array of two or more possible nodes of a clinical decision support tree, wherein at least one of the two or more nodes indicates cardiopulmonary resuscitation (CPR) treatment of the patient with no ventilation, and wherein at least another of the two or more possible nodes indicates CPR treatment of the patient with active ventilation; determining which of the two or more possible nodes to emphasize based on the SmO2 level; and updating the array of the two or more possible nodes based on the determination.

A method as described in one or more of the above paragraphs, further comprising: monitoring a pH level of a muscle of the patient, wherein determining which of the two or more possible nodes to emphasize based on the SmO2 level comprises determining which of the two or more possible nodes should be emphasized based on the SMO2 level and the pH level.

A method as described in one or more of the above paragraphs, wherein updating the array comprises visually emphasizing a determined node of the array of the two or more possible nodes based on the determination.

A method as described in one or more of the above paragraphs, wherein visually emphasizing the determined node includes changing a color of the determined node.

A method as described in one or more of the above paragraphs, wherein visually emphasizing the determined node includes changing a size of the determined node.

A method as described in one or more of the above paragraphs, wherein visually emphasizing the determined node includes changing a shape of the determined node.

A method as described in one or more of the above paragraphs, wherein updating the array comprises visually emphasizing a determined node of the array of the two or more possible nodes based on the determination.

A method as described in one or more of the above paragraphs, wherein visually emphasizing the determined node includes changing a color of the determined node.

A method as described in one or more of the above paragraphs, wherein visually emphasizing the determined node includes changing a size of the determined node.

A method as described in one or more of the above paragraphs, wherein visually emphasizing the determined node includes changing a shape of the determined node.

A medical system according to an embodiment of the present invention includes at least one sensor configured to monitor end tidal carbon dioxide (ETCO2) level of a patient who is undergoing cardiac arrest and to generate a signal representing the ETCO2 level; a user interface device; a processor communicably coupled to the user interface device, the processor configured to: cause the user interface device to present an array of two or more possible nodes of a clinical decision support tree, wherein at least one of the two or more possible nodes indicates cardiopulmonary resuscitation (CPR) treatment of the patient with no ventilation, and wherein at least another of the two or more possible nodes indicates CPR treatment of the patient with active ventilation; determine which of the two or more possible nodes should be emphasized based on the ETCO2 level; and update the array of the two or more possible nodes based on the determination.

A medical system as described in one or more of the above paragraphs, wherein the processor is further configured to update the array by visually emphasizing the one of the two or more possible nodes that should be emphasized as compared to an other of the two or more possible nodes.

A medical system as described in one or more of the above paragraphs, wherein visually emphasizing the one of the two or more possible nodes includes changing a color of the one of the two or more possible nodes.

A medical system as described in one or more of the above paragraphs, wherein visually emphasizing the one of the two or more possible nodes includes changing a size of the one of the two or more possible nodes.

A method for clinical decision support in a cardiac arrest medical response according to an embodiment of the present invention includes monitoring an end tidal carbon dioxide (ETCO2) level of a patient who is undergoing cardiac arrest; generating a signal representing the ETCO2 level; displaying on a user interface device an array of two or more possible nodes of a clinical decision support tree, wherein at least one of the two or more nodes indicates cardiopulmonary resuscitation (CPR) treatment of the patient with no ventilation, and wherein at least another of the two or more possible nodes indicates CPR treatment of the patient with active ventilation; determining which of the two or more possible nodes to emphasize based on the ETCO2 level; and updating the array of the two or more possible nodes based on the determination.

A medical system according to an embodiment of the present invention includes at least one sensor configured to monitor pH level of a patient who is undergoing cardiac arrest and to generate a signal representing the pH level; a user interface device; a processor communicably coupled to the user interface device, the processor configured to: cause the user interface device to present an array of two or more possible nodes of a clinical decision support tree, wherein at least one of the two or more possible nodes indicates cardiopulmonary resuscitation (CPR) treatment of the patient with no ventilation, and wherein at least another of the two or more possible nodes indicates CPR treatment of the patient with active ventilation; determine which of the two or more possible nodes should be emphasized based on the pH level; and update the array of the two or more possible nodes based on the determination.

A method for clinical decision support in a cardiac arrest medical response according to embodiments of the present invention includes monitoring a pH level of a patient who is undergoing cardiac arrest; generating a signal representing the pH level; displaying on a user interface device an array of two or more possible nodes of a clinical decision support tree, wherein at least one of the two or more nodes indicates cardiopulmonary resuscitation (CPR) treatment of the patient with no ventilation, and wherein at least another of the two or more possible nodes indicates CPR treatment of the patient with active ventilation; determining which of the two or more possible nodes to emphasize based on the pH level; and updating the array of the two or more possible nodes based on the determination.

A medical system according to an embodiment of the present invention includes at least one sensor configured to monitor a muscle oxygen saturation (SmO2) level of a patient who is undergoing cardiac arrest and to generate a signal representing the SmO2 level; a user interface device; a processor communicably coupled to the user interface device, the processor configured to: compare the SmO2 level over time with a predetermined threshold level; and indicate via the user interface device whether further cardiopulmonary resuscitation attempts are likely to be successful, based on the SmO2 level.

A medical system according to an embodiment of the present invention includes: at least one sensor configured to monitor end tidal carbon dioxide (ETCO2) level of a patient who is undergoing cardiac arrest and to generate a signal representing the ETCO2 level; a user interface device; a processor communicably coupled to the user interface device, the processor configured to: compare the ETCO2 level over time with a predetermined threshold level; and indicate via the user interface device whether further cardiopulmonary resuscitation attempts are likely to be successful, based on the ETCO2 level.

A medical system according to an embodiment of the present invention includes: at least one sensor configured to monitor a pH level of a patient who is undergoing cardiac arrest and to generate a signal representing the pH level; a user interface device; a processor communicably coupled to the user interface device, the processor configured to: compare the pH level over time with a predetermined threshold level; and indicate via the user interface device whether further cardiopulmonary resuscitation attempts are likely to be successful, based on the pH level.

A medical system according to an embodiment of the present invention includes: at least one sensor configured to monitor a hematocrit level of a patient who is undergoing cardiac arrest and to generate a signal representing the hematocrit level; a user interface device; a processor communicably coupled to the user interface device, the processor configured to: compare the hematocrit level over time with a predetermined threshold level; and indicate via the user interface device whether one or both of a frequency and an intensity of ventilation measures applied to the patient should be adjusted, based on the hematocrit level.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 5 is a table describing a differential diagnosis outline for acute dyspnea in adults.

FIG. 6 is a table describing clues to the diagnosis of dyspnea.

FIG. 7 is a table listing physical examination findings in the diagnosis of acute dyspnea.

FIG. 13 illustrates an example trauma assessment protocol.

FIG. 14 illustrates an example rapid trauma assessment protocol.

FIG. 15 illustrates an example focused physical exam protocol.

FIG. 16 illustrates an example amputation injuries protocol.

FIG. 17 illustrates an example bleeding control protocol.

FIG. 18 illustrates an example burns protocol.

FIG. 19 illustrates an example electrocution protocol.

FIG. 20 illustrates an example spinal immobilization protocol.

FIG. 22 illustrates an example multi-system trauma protocol.

FIG. 23 illustrates an example near drowning protocol.

FIG. 24 illustrates an example trauma in pregnancy protocol.

FIG. 25 illustrates an example traumatic cardiac arrest protocol.

Figure 1:
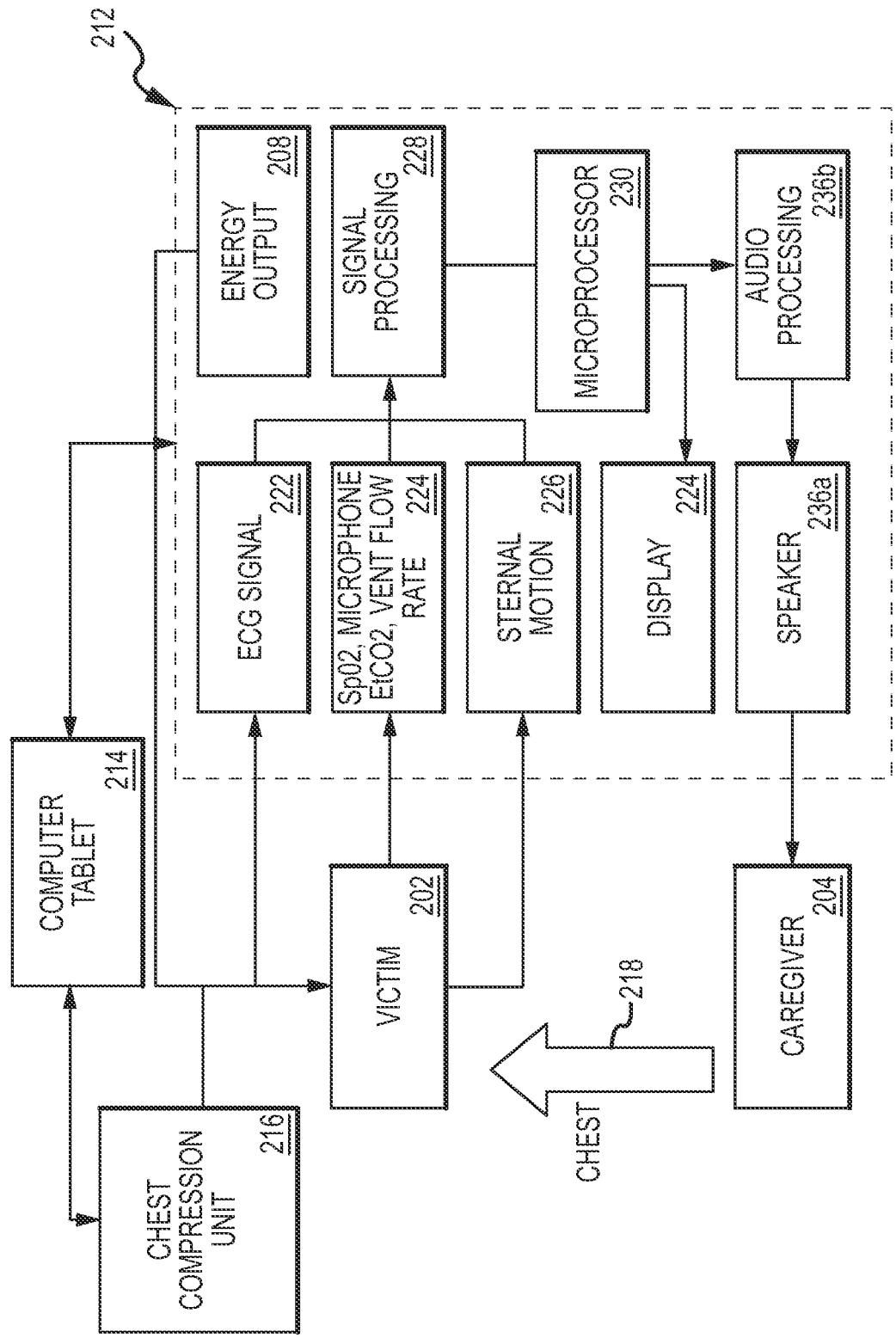
FIG. 1 illustrates a clinical decision support system, according to embodiments of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 2:
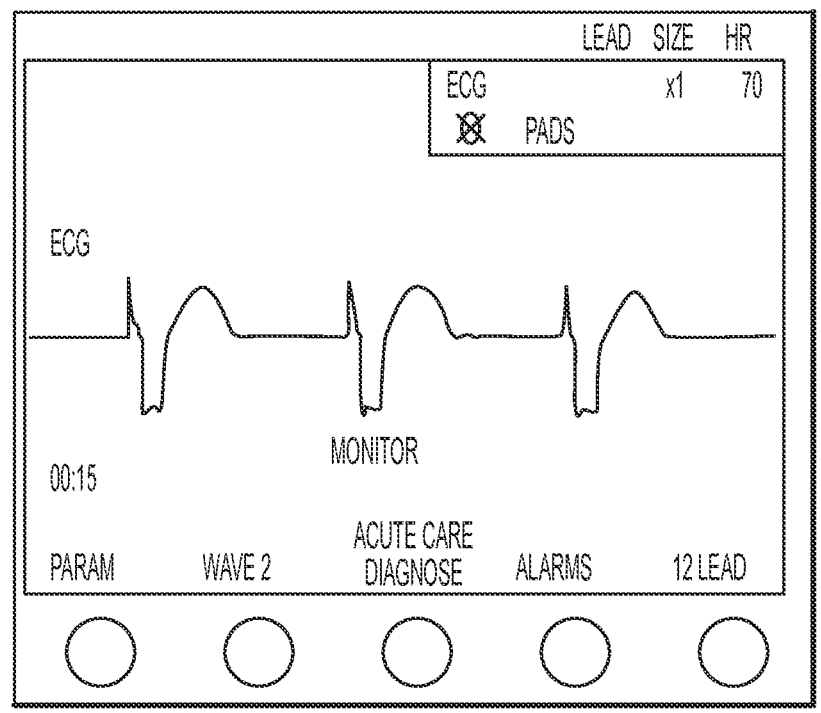
FIG. 2 illustrates a user interface for a medical device, according to embodiments of the present invention.

FIG. 1 shows a block diagram of the system, according to embodiments of the present invention. In one embodiment, a combined defibrillator/monitor device such as the E-Series manufactured by ZOLL Medical of Chelmsford Mass. has keys whose labeling is provided by on-screen text. The text is thus configurable in real time ether due to input by the user or as a result of analysis and decision making by the defibrillator or other devices with which the defibrillator is in communication at the time of the defibrillator's use, such as the computer tablet device 214 or remote base station staffed by medical dispatch or medical supervisory personnel in communication with the computer tablet. The computer tablet may take the form of an iPad (Apple Corp., Cupertino Calif.). Such screen-labeled keys may be referred to as "soft-keys". A specific soft-key is initially labeled "Acute Care diagnose" at device turn-on as shown in FIG. 2, according to embodiments of the present invention. Upon detecting a key press of the Acute Care Diagnose key, the defibrillator changes the functionality and labeling of the keys to those shown in FIG. 3. These five labels—"Respiratory Distress" or alternatively "Dyspnea", "Altered Mental Status", "Cardiac Distress", "Trauma" and "Pain/Abnormal Nerve Sensation"—differ from the traditional symptoms associated with differential diagnosis in that they identify classes of patients and potential workflows and diagnosis and treatment pathways (DTP), and are listed in relative frequency with which paramedics and other emergency personnel encounter patients meeting these criteria in actual practice.

Figure 4:
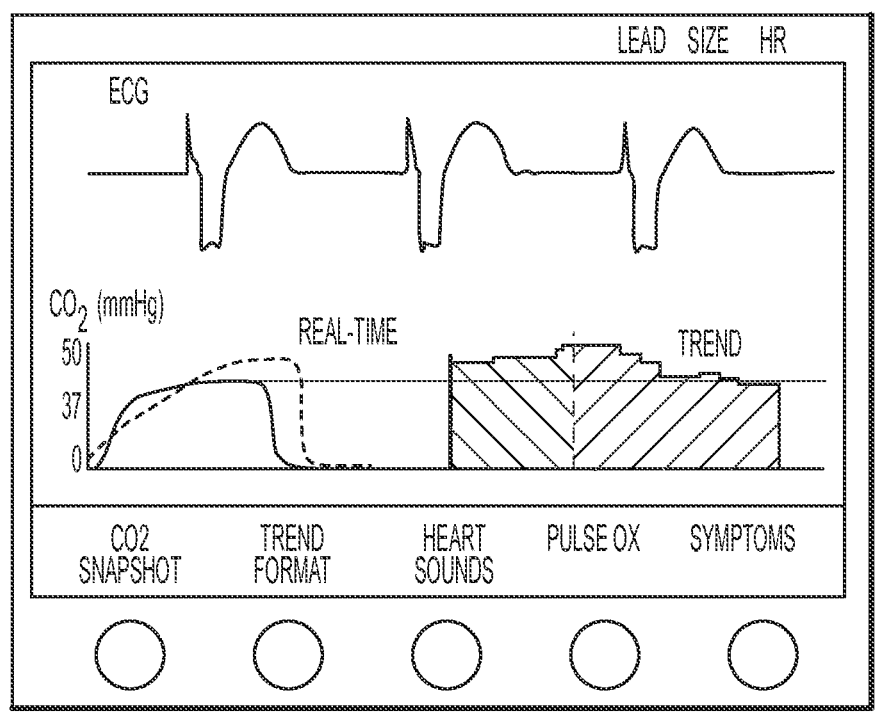
FIG. 4 illustrates the user interface of FIGS. 2 and 3 upon selection of a respiratory distress mode, according to embodiments of the present invention.

By pressing the soft-key for each DTP, the defibrillator is then configured to potentially activate certain physiological sensors and display the sensor data in such a way as to provide the caregiver the optimal information, presented in the optimal fashion so as to diagnose and treat the patient most accurately and efficiently. Each DTP may include a template according to which sensor data, or the physiological and/or measurement data derived therefrom, is displayed in a way most useful and/or efficient for that particular DTP. For instance, if the "Respiratory Distress" soft-key is pressed, then the waveforms and numeric physiologic data on the screen change to that shown in FIG. 4. Stored snapshots of individual CO2 breath waveforms may be initiated via the CO2 Snapshot soft-key. These snapshots remain on the display for reference to the clinician both for automating measurements for diagnosis as well as for assessing the effectiveness of a particular therapy.

Figure 8A:
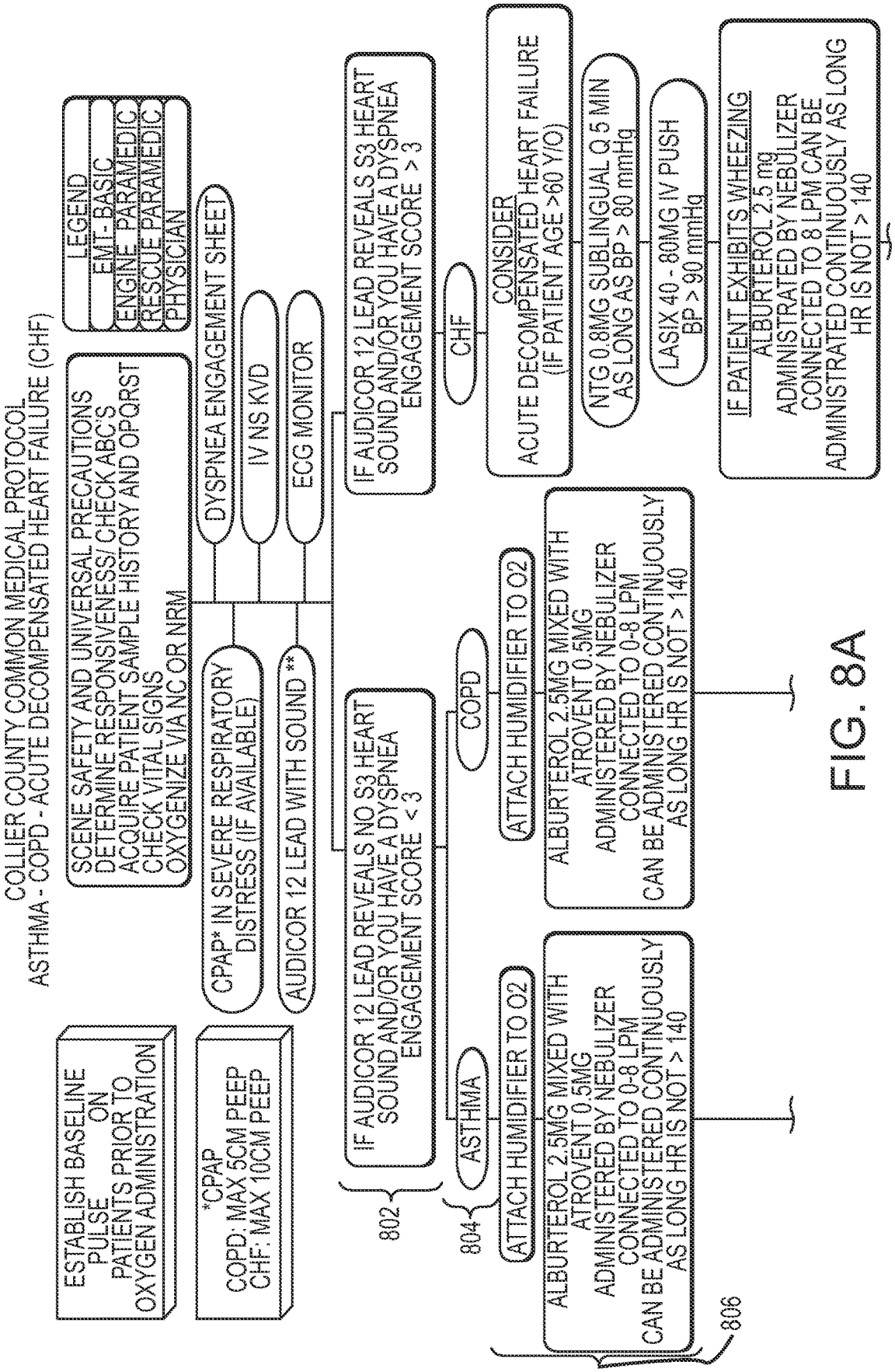
FIG. 8A is a top portion of a common medical protocol and differential diagnosis flow chart for adult shortness of breath.
Figure 8B:
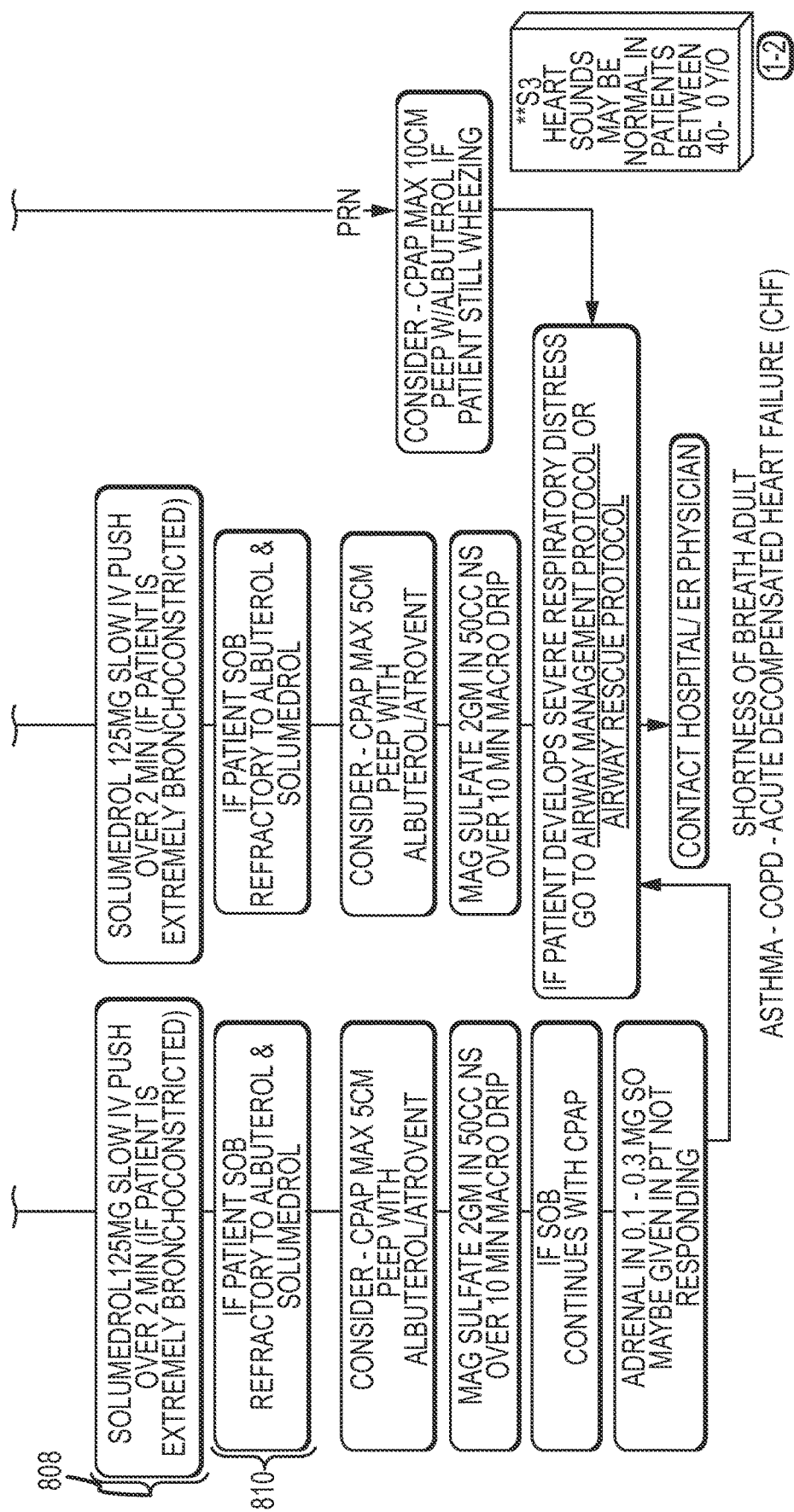
FIG. 8B is a continuation of the common medical protocol and differential diagnosis flow chart of FIG. 8A.
Figure 9:
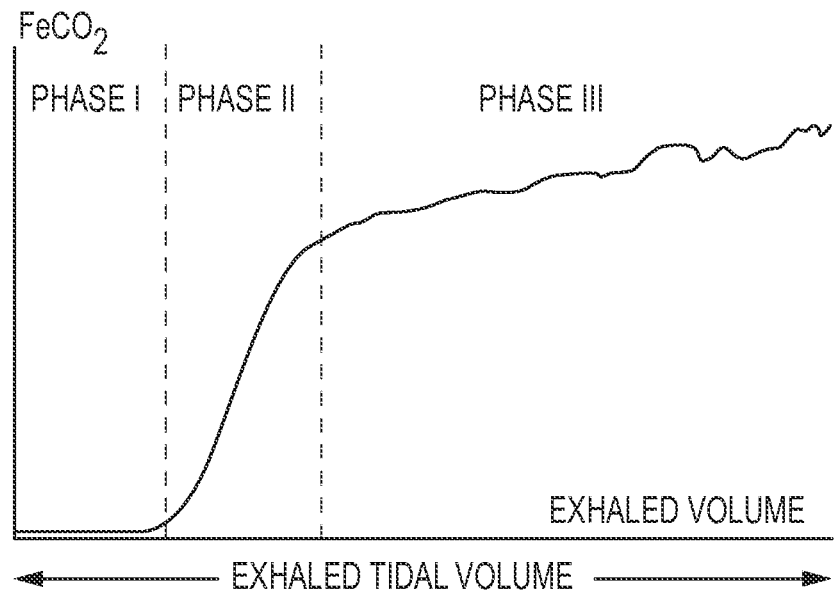
FIG. 9 illustrates a carbon dioxide snapshot waveform which may be displayed on the user interface when selected by the user, according to embodiments of the present invention.

Heart sound measurement and detection may be incorporated into the monitoring device for the detection of S3 and S4 heart sounds and automatically narrow the differential, or suggest for the rescuer to confirm agreement with the software diagnosis, of heart failure or pulmonary edema. A flowchart for evaluating heart sounds is shown in FIGS. 8A and 8B. Pulse oximetry and capnography are also very helpful measures and may be automatically incorporated into the algorithm for more accurate diagnosis. The same sensors used to detect heart sounds may also be employed to detect breath sounds and to analyze their quality. Specific algorithms may be employed to detect wheezing, crackles, rale or stridor, each of which may be indicative of a particular disease.

Sensors such as flow sensors and O2 gas sensors are included in some embodiments, so that the additional physiological measurements such as volumetric Co2, volumetric O2 and spirometry, which are relevant for diagnosis and treatment of dyspnea, may be included and displayed on the Respiratory Distress DTP screen. An oxygen sensor may be located in the patient's airway, which may assist in calculating the metabolic needs of the patient.

Figure 10:
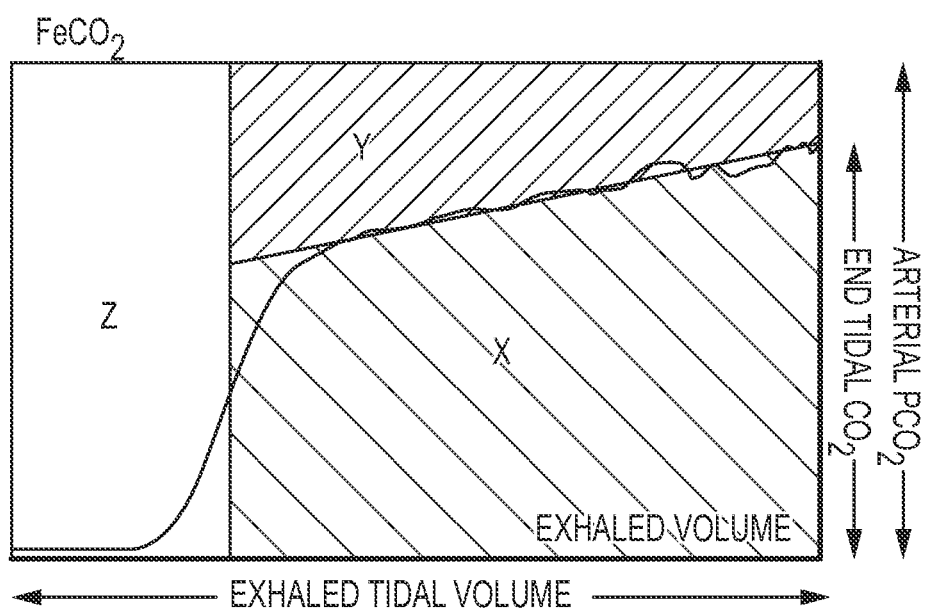
FIG. 10 illustrates the carbon dioxide snapshot waveform of FIG. 9 with displayed measurements, according to embodiments of the present invention.

The display on the defibrillator 212 is a touchscreen, according to some embodiments of the present invention. The caregiver can easily initiate measurements such as on the CO2 snapshot waveform or the spirometry snapshot waveform via touchscreen gesture such as a double tap. A zoom icon may exist in the upper corner of each waveform box, such as the CO2 snapshot, such that when the zoom button is touched, that particular waveform fills the display of the defibrillator. Another measurement button is present which, when touched, displays all the relevant measurements for a particular waveform, according to embodiments of the present invention. A gestural interface is provided as part of the touchscreen. Using two fingers or finger and thumb to touch to two points in the waveform (which may also be referred to as a "caliper" measurement or gesture) will cause measurements to be displayed and/or overlaid onto the physiological data, as illustrated in FIG. 10. For instance, dead space volume, phase II and III slopes which are indicative of COPD, and estimates of arterial pCO2 may be listed on the screen after initiation of CO2 waveform measurement.

According to embodiments of the present invention, the processor communicably coupled with the touchscreen portion of a decision support system may be configured to recognize the wave shape of a wave signal being displayed, and/or recognize the edge of an image being displayed, in order to improve the accuracy of a caliper touch gesture. For example, if a user were to use a caliper gesture to measure or "zoom in" on an ST elevation in an ECG wave display, the decision support system may be configured to recognize that if one of the user's fingers taps just below the top of the ECG wave, that the user likely intended to include the top of the ECG wave in the enlarged or selected view. In addition, the decision support system may be configured to permit an ability to enlarge (zoom) and adjust measurement points individually using the touchscreen. A tap/click and drag method may be used to set the caliper gesture; for example, to hone in on a particular portion of displayed waveform, the user may press on one point and drag to another point to indicate the endpoints of the caliper gesture.

Specific out-of-range readings can be displayed in red or highlighted by other mechanisms, such as bold-face font and/or flashing. Touching the highlighted values will cause the display to show the possible diagnoses which are consistent with the measurements, according to embodiments of the present invention. A specific graphical zone of the screen can be designated with a graphical image of the computer tablet. By dragging waveforms, measurements, or any other data object shown on the display over onto the computer tablet icon, it can automatically be presented on the computer tablet that is linked to the defibrillator.

Capnography is helpful in the assessment of asthma, where an increased slope in the expiratory plateau provides a measure of bronchospasm. The slope of the plateau phase (phase III) provides a measure of airway obstruction. The adequacy of b-agonist bronchodilatory therapy for an asthma exacerbation may be monitored through observation of slope change of phase III.

As referenced in U.S. Patent Application Publication No. 2011/0172550, published on Jul. 14, 2011, which is incorporated by reference herein in its entirety for all purposes, the data for the patient's history may be entered via the computer tablet with patient physiological measures via the monitor. As the differential diagnosis often implicates both patient history, patient examination findings along with measures of the patient's physiological state via such monitoring as ECG, capnography and pulse oximetry, these data elements are integrated into a user interface that automatically or semi-automatically integrates the various data elements on a single differential diagnosis screen within the application on the computer tablet. The interface may begin by asking the rescuer to choose from a list of common presenting symptoms or complaints by the patient, for example dyspnea or respiratory distress. The information such as on the screens of FIGS. 5, 6, and 7 (taken from Am Fam Physician 2003; 68:1803-10) provides one possible structured approach for rescuers to obtain information. As patient history and physical examination findings are entered on the computer tablet, the differential diagnosis page will gradually narrow down the possible diagnoses.

Figure 11:
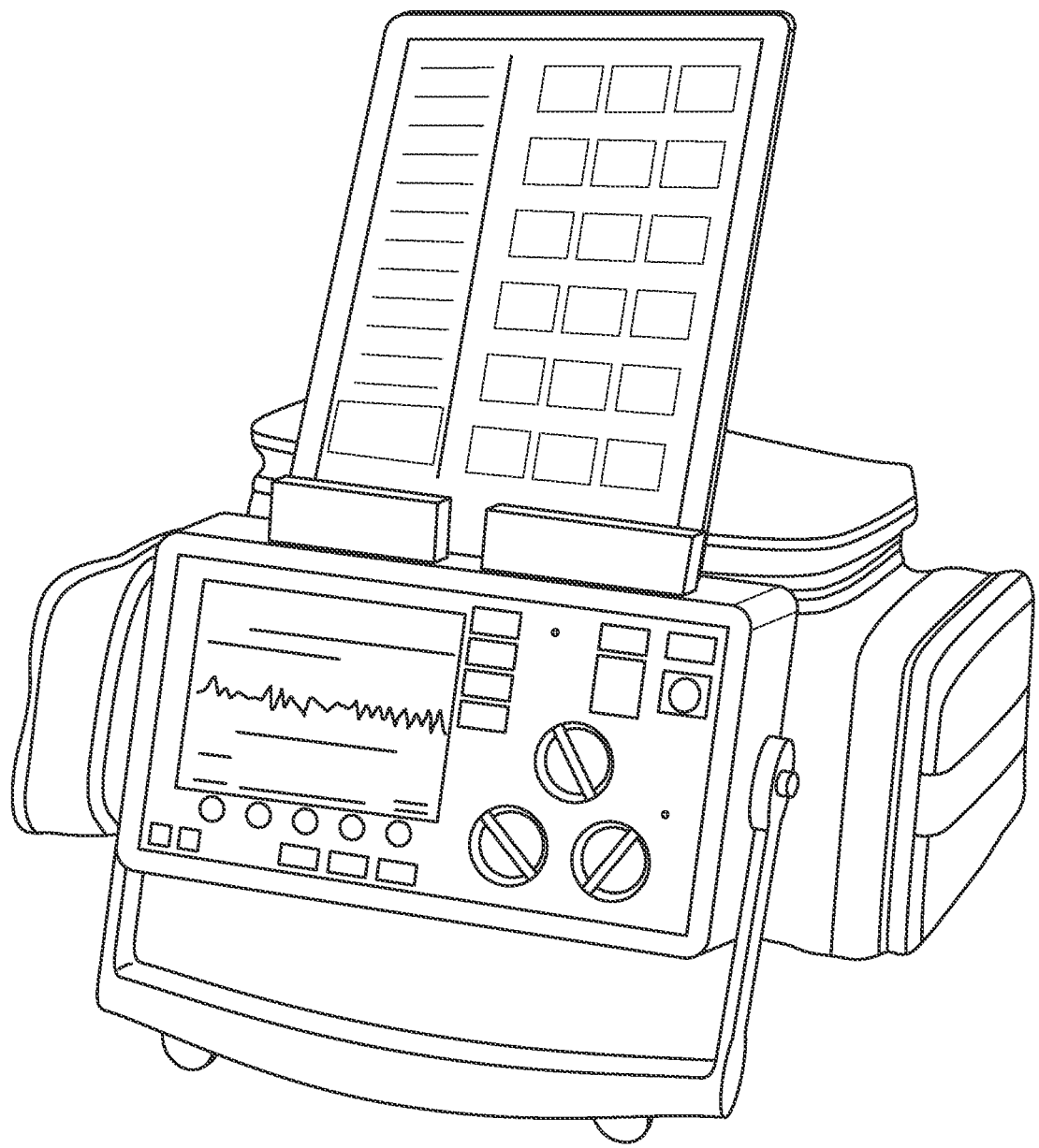
FIG. 11 illustrates a tablet computing device docked on a defibrillator device, according to embodiments of the present invention.

In another embodiment, the defibrillator contains a docking feature for propping up a computer tablet such as an Apple® iPad® on top of the defibrillator in a stable position via mounting features integrated onto the defibrillator, as illustrated in FIG. 11. Other mobile computing devices, including tablet computers, an iPhone®, an iTouch®, and other touchscreen monitors may be used. Alternatively, a low power, battery powered, touchscreen monitor may be used, such as, for example, those that transfer information to and from a computing device via a wired or wireless USB connection. Communication may be provided wirelessly between the two devices (the medical device and the mobile computing device, for example). Other communicable coupling may be achieved between the two devices; for example, wired. The iPad may include a protective housing and/or waterproof housing to protect it from the typical physical abuse it would likely encounter in the prehospital environment. Mounting features integral to such an iPad housing allow it to be easily attached on top of the defibrillator on scene. The mounting feature on the defibrillator may be able to hinge to allow the iPad® to hinge down when not in use into a protective pocket on the defibrillator. The iPad® may also be undocked and used nearby to the defibrillator, without need for physical connection. A physical slot may also be provided, preferably at the side, top or back of the unit that allows for the iPad® to have its battery charged by the defibrillator. Internal to the frame of the iPad® protective housing is the standard iPad® connector, while on the exterior of the frame of the iPad® protective housing are much more robust mechanical and electrical connections that can withstand the extensive abuse experienced by medical devices in the prehospital emergency setting, according to embodiments of the present invention.

The results of this integrated analysis of physiological data, patient history and examination findings may then be displayed on the defibrillator, potentially in the form of asking to make an additional physiological measurement. The results of this integrated analysis of physiological data, patient history and examination findings may alternatively, or additionally, be displayed on the tablet computer. According to some embodiments of the present invention, the tablet computer, or other mobile computing device, may be communicably coupled with the defibrillator or other physiological assessment device, for example through a wireless connection. As used herein, the phrase "communicably coupled" is used in its broadest sense to refer to any coupling whereby information may be passed. Thus, for example, communicably coupled includes electrically coupled by, for example, a wire; optically coupled by, for example, an optical cable; and/or wirelessly coupled by, for example, a radio frequency or other transmission media. "Communicably coupled" also includes, for example, indirect coupling, such as through a network, or direct coupling.

According to embodiments of the present invention, a user interface device is communicably coupled to a processor, and the processor is configured to receive data entered via the user interface device, as well as data received from one or more sensors, in order to perform clinical decision support based on both data sources. The user interface device may include one or more devices such as a touch screen computer, a tablet computer, a mobile computing device, a smart phone, an audio receiver, an audio transmitter, a video receiver, a video transmitter, a camera, and a "heads up" display projected onto a user's glasses or face shield. A small monitor may be mounted onto eyeglasses, a face shield, and/or integrated with other wearable communications devices, such as, for example, an ear bud or a Bluetooth® hands free phone adaptor. The user interface device may include a combination of devices for conveying options and receiving input; for example, an audio speaker may be used to convey possible DTPs, and an audio receiver may be used to receive a verbal command indicating a selection of one of the DTPs. Instead of an audio receiver, a video camera may be used to receive a gestural command that will be interpreted by the processor as a selection of one of the possible DTPs, or input elements. Using hands-free devices for user interface devices may free the hands of a caregiver to perform clinical tasks, while still permitting non-intrusive decision support and/or differential diagnosis for the caregiver.

FIGS. 8A and 8B illustrate a differential diagnosis and/or clinical support process through which a computer processor may take a caregiver, using the user interface device, according to embodiments of the present invention. For example, if the caregiver selected "Respiratory Distress" from among the five DTPs presented on the screen of FIG. 3, then the user interface device would prompt the caregiver to input information about step 802 in the flowchart of FIG. 8, which flows from top to bottom. At step 802, if the 12-lead reveals an S3 heart sound, or if the Dyspnea Engagement Score is greater than 3, then the decision support system will take the user through the Acute Decompensated Heart Failure (CHF) decision/diagnosis process.

The decision support system may take into account both physiological data received from sensors, and information data received from the caregiver (e.g. via mobile computing device such as an iPad®), in helping the caregiver move from one decision point in the flow chart to the next, while updating any display or information provided along the way. For example, the decision support system may indicate to the user that, based on processing of the ECG data, there does not appear to be an S3 heart sound present, and ask the caregiver to confirm this assessment. The decision support system may also, or alternatively, request the caregiver to enter a Dyspnea Engagement Score, or suggest one for confirmation by the caregiver. At step 802, if the 12-lead reveals no S3 heart sound, or if the Dyspnea Engagement Score is less than 3, then the decision support system will recognize that the caregiver is not dealing with a CHF situation, but then moves to step 804 in which the decision support system changes its display and/or input prompts in order to help the caregiver determine whether to enter the Asthma treatment path or the COPD treatment path.

Again, the decision support system may factor in various physiological data from sensors, as well as various informational data received about the particular patient, in helping to support the caregiver's decision. For example, as illustrated in FIG. 6, if the patient information (either entered by the caregiver or obtained from another source) indicates that the patient is involved in heavy tobacco use, the decision support system will recognize at step 804 that a COPD diagnosis is more likely, whereas if the caregiver indicates to the decision support system that the patient is experiencing a cough, or has a history of asthma, the decision support system may recognize at step 804 that an Asthma diagnosis is more likely. In addition to, or alternatively to, the informational diagnosis support reflected in FIG. 6, the decision support system may gather findings using physiological data to help the caregiver determine the appropriate treatment path. For example, if a breathing or breath sound sensor generates data that, when processed, indicates clubbing, barrel chest, or decreased breath sounds, the decision support system may recognize at step 804 that a COPD treatment path is more appropriate, whereas if the breath sound sensor generates data indicative of pulsus paradoxus, or if a muscle activity sensor indicates accessory muscle use, the decision support system may recognize at step 804 that an Asthma treatment path is more appropriate.

According to embodiments of the present invention, the decision support system may suggest or propose a diagnosis or treatment path, for example by indicating statistical probabilities (based on charts and data such as those of FIGS. 6 and 7) or relative likelihoods, and ask for confirmation or final selection by the caregiver. For example if at step 804 the decision support system receives confirmation of an Asthma diagnosis, then the user interface device may change the information presented to the caregiver, for example by launching into a treatment protocol specific to the Asthma diagnosis. At step 806, the decision support system may suggest that the caregiver attach a humidifier to the patient's oxygen supply, and administer 2.5 milligrams of albuterol mixed with 0.5 milligrams of Atrovent administered by nebulizer connected to a 6-9 liter per minute source, and may indicate that the dosage may be administered continuously as long as the heart rate is not greater than 140. The decision support system may monitor the heart rate, and give a visual and/or audio indication when and if the heart rate reaches or approaches 140, in this example.

At step 808, the decision support system may help the caregiver decide whether the patient is extremely bronchoconstricted, for example by showing data or measurements related to blood oxygen content, respiration rate, or respiration volume. Upon a confirmation by the caregiver that the patient is extremely bronchoconstricted at step 808, the decision support system may then suggest to the caregiver that a 125 milligram dose of Solumedrol be administered over a slow (e.g. 2 minute) intravenous push. At step 810, the decision support system may help the caregiver to decide whether the patient's symptoms have improved (e.g. whether the patient's shortness of breath has improved with the treatment thus far). For example, the decision support system may display and/or analyze the patient's end-tidal waveform, and suggest that the patient does not appear to be responding to the treatment, and ask for the caregiver's confirmation. If the caregiver confirms the decision, then the decision support system may continue to guide the caregiver through additional treatment options, for example those indicated in FIG. 8. In this way, the decision support system guides the caregiver through complex decisionmaking processes, during the clinical encounter, using both physiological data and informational data gathered from the patient or input by the caregiver, in a way which would be too inconvenient or time-consuming for the caregiver to perform absent the decision support system.

The decision support according to embodiments of the present invention may or may not be fully automated. Inference engines utilizing Bayesian networks, neural networks, genetic algorithms, or simpler rule-based systems may be employed.

In another embodiment, the tissue CO2 or pH are measured by methods such as those described in U.S. Pat. No. 6,055,447, which describes a sublingual tissue CO2 sensor, or U.S. Pat. Nos. 5,813,403, 6,564,088, and 6,766,188, which describe a method and device for measuring tissue pH via near infrared spectroscopy (NIRS), and which are all incorporated herein by reference in their entirety for all purposes. NIRS technology allows the simultaneous measurement of tissue PO2, PCO2, and pH. One drawback of previous methods for the measurement of tissue pH is that the measurements provided excellent relative accuracy for a given baseline measurement performed in a series of measurements over the course of a resuscitation, but absolute accuracy was not as good, as a result of patient-specific offsets such as skin pigment. One of the benefits achieved by some embodiments of the present invention is the elimination of the need for absolute accuracy of these measurements, and the reliance on only the offset and gain being stable over the course of the resuscitation. Tissue CO2 and pH are particularly helpful in monitoring in the trauma DTP. Physiological parameters on display for the trauma DTP may be one or more of: invasive and non-invasive blood pressure, tissue CO2 and pH, ECG, SpO2 trending, and heart rate variability risk index. The ECG may be analyzed to determine the interval between adjacent R-waves of the QRS complexes and using this interval to calculate heart rate variability as a running difference between adjacent R-R intervals. It is known to those skilled in the art that an abrupt reduction in variability will often precede by many minutes a precipitous decline in a patient's blood pressure (traumatic arrest). By monitoring the trend in heart rate variability, the traumatic arrest can be anticipated and prevented.

Figure 12:
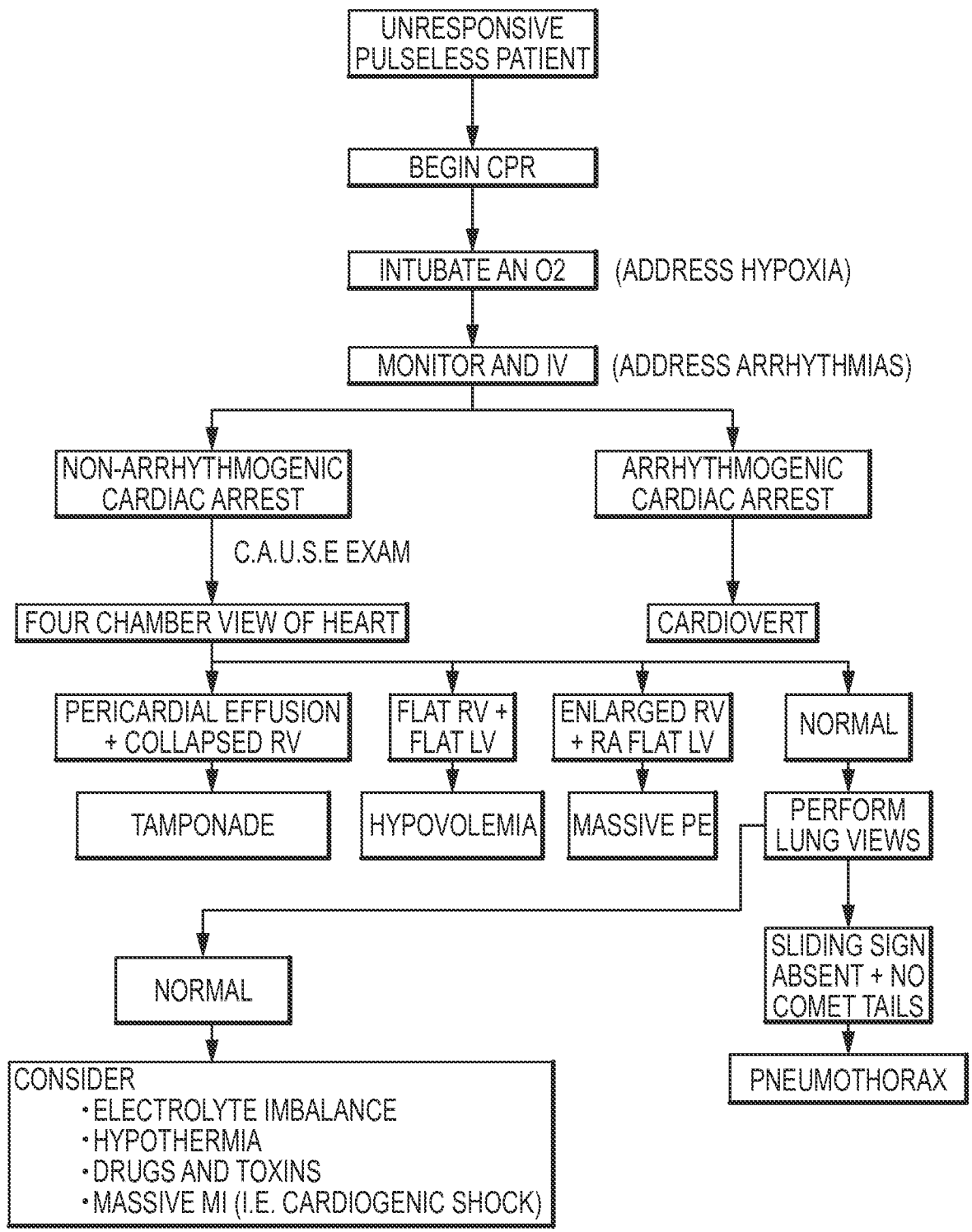
FIG. 12 illustrates a protocol for use in patients with cardiac arrest.
Figure 21:
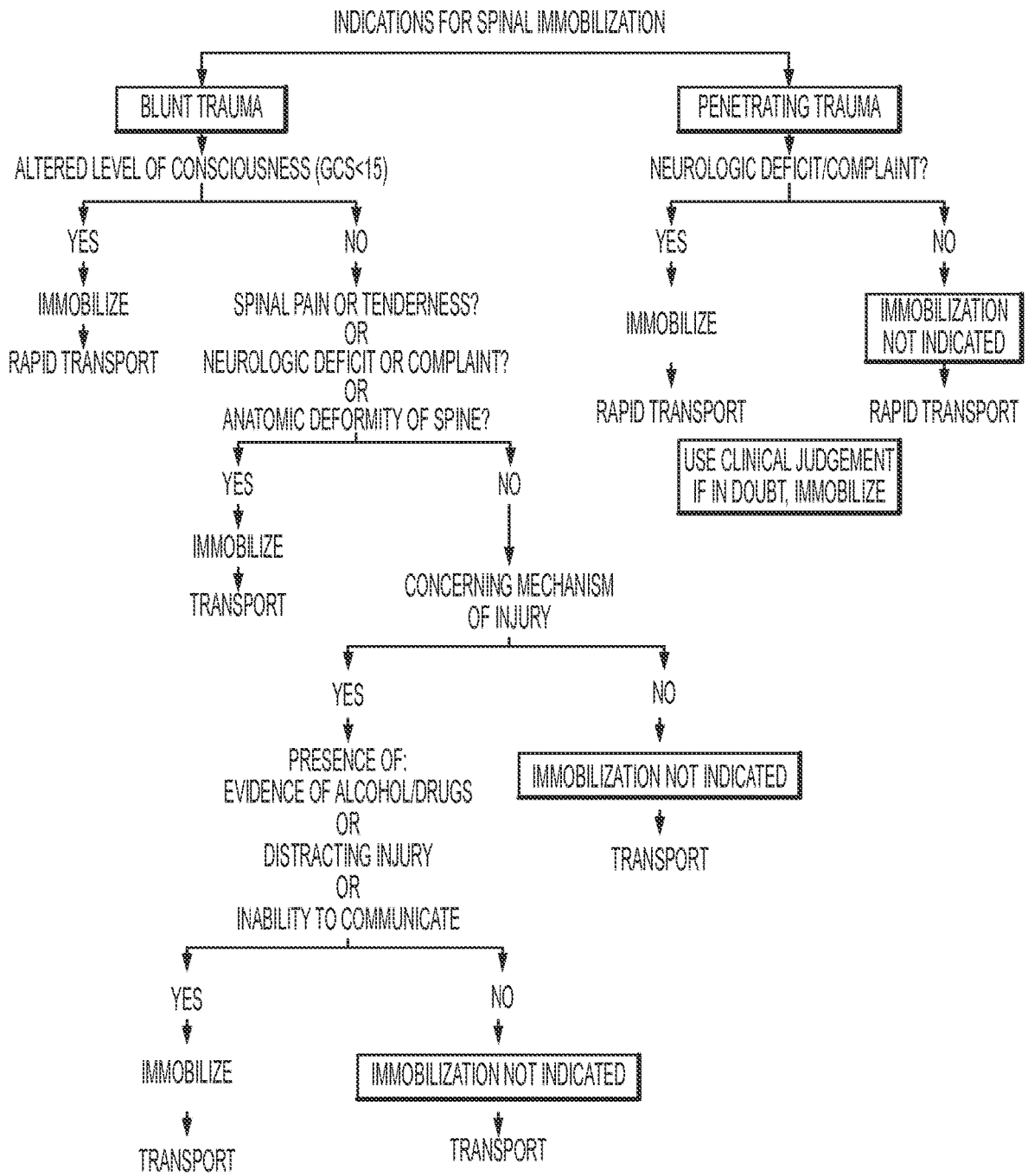
FIG. 21 illustrates additional steps in the spinal immobilization protocol of FIG. 20.

Another sensor of use for the trauma DTP is ultrasound, according to embodiments of the present invention. According to C. Hernandez et al., C.A.U.S.E.: Cardiac arrest ultra-sound exam—A better approach to managing patients in primary non-arrhythmogenic cardiac arrest, Resuscitation (2007), doi:10.1016/j.resuscitation.2007.06.033, which his incorporated by reference herein in its entirety for all purposes:

C.A.U.S.E. is a new approach developed by the authors. The C.A.U.S.E. protocol addresses four leading causes of cardiac arrest and achieves this by using two sonographic perspectives of the thorax; a four-chamber view of the heart and pericardium and anteromedial views of the lung and pleura at the level of the second intercostal space at the midclavicular line bilaterally. The four-chamber view of the heart and pericardium is attained using either the subcostal, parasternal or apical thoracic windows. This allows the individual performing the examination to select the most adequate view depending on the patients' anatomy. The authors recommend beginning with the subcostal view first as this view makes it possible for the practitioner to evaluate the heart without interrupting chest compression. If this view is not possible then the apical or parasternal approaches may be used during coordinated pulse checks lead by the resuscitation team leader. A four-chamber view is used in this protocol as it allows for ease of comparison between the different chambers in the heart, facilitating the diagnosis of hypovolemia, massive PE, and cardiac tamponade (FIG. 6). Pneumothorax is diagnosed by identifying the lack of sliding sign and comet-tail artifact while looking in the sagital plane at the second intercostal space of the midclavicular line (FIG. 7). For both the cardiac and lung views it is recommended to use a 2.5-5.0 phased array transducer probe. This allows the examiner to use the same probe for both lung, heart and if needed abdominal exam. This type of probe was used by Knudtson in his study involving ultrasound for the use of identifying pneumothorax as an addition to the FAST exam, and it yielded very a high accuracy in detecting pneumothorax, yet still remained useful in identifying the heart and abdominal organs. The protocol is best described in diagram form. [see FIG. 12]

The caregiver selecting elements of the flowchart results in the ultrasound sensor being activated and images presented on the computer tablet. Additional instructions can be requested from the interface on either the computer tablet and/or the defibrillator. Based on the selections and instructions, the settings of the ultrasound can be adjusted to deliver the optimal images, according to embodiments of the present invention.

Figure 3:
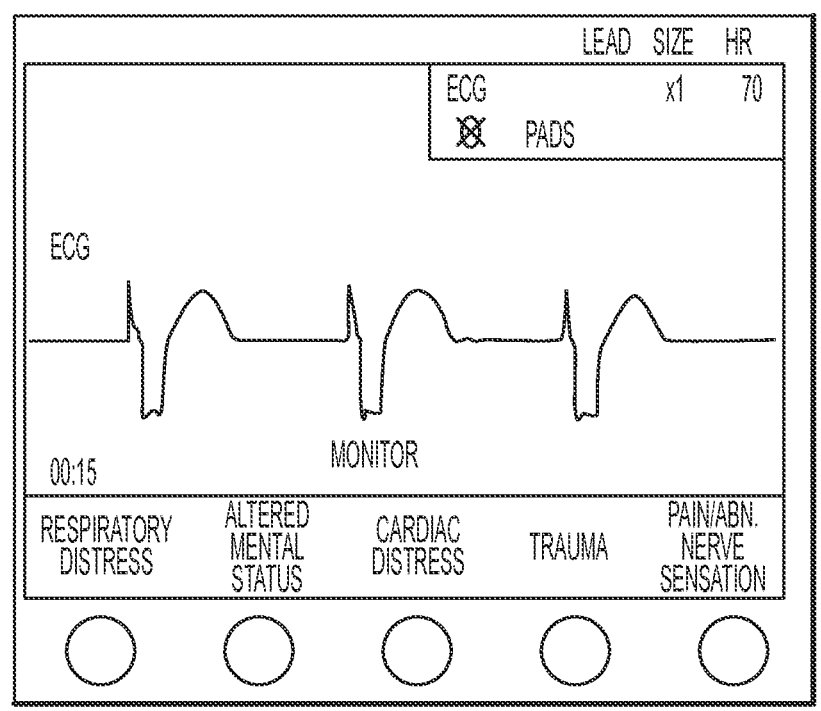
FIG. 3 illustrates the user interface of FIG. 2 upon selection of an acute care diagnosis mode, according to embodiments of the present invention.

Although five diagnosis and treatment pathways are discussed with respect to FIG. 3, the differential diagnosis/decision support system may be configured to support decisionmaking and diagnosis with respect to other DTPs, and may be configured to display and support various combinations of one or more DTPs, from among the five shown in FIG. 3 and others. According to other embodiments of the present invention, each user may configure the decision support system to use customized DTP for each DTP option; for example, the user may change the default series of questions/steps/readings for the Trauma DTP with a new series of questions/steps/readings based on caregiver-specific, patient-specific, geography-specific, and/or regulation-specific treatment protocols. In this way, the decision support system according to embodiments of the present invention operates to guide decision-making and diagnosis for a caregiver in a way that accommodates various kinds of DTPs.

For example, if a user selected the Trauma DTP option from the screen of FIG. 3, the decision support system may be configured to guide a user through a decision and treatment pathway similar to that shown in FIGS. 13-25. The user would then be presented with a series of further options, such as "amputation injury," "bleeding control," "burns," and the like. Selecting one of these further options would then cause the decision support system to enter and display the particular pathway or pathways relevant to the selected option. According to embodiments of the present invention, the decision support system is comprised by a user interface device, independent of a medical device or one or more sensors, in a way which simply guides the caregiver through a series of decisions according to a pre-established flow chart. At a basic level, a medical device, such as a defibrillator, may include one or more decision support flow charts and/or treatment protocols, which guide the caregiver through various decisions, either with or without sensor data or other data input. A graphical DTP may be included in a defibrillator device as a reference document, electronically navigable.

According to other embodiments, the decision support system is informed by a combination of caregiver observations, patient information, and/or sensor data. Assessment and/or scoring may be performed, either by receiving data from the caregiver, or receiving data from sensors, or both. For example, for a trauma DTP, the decision support system may take into account pulse rate, breathing data, qualitative breathing data, pulse rate, blood loss, blood pressure, presence of broken limbs, and/or compound fractures. Or, in a cardiac distress DTP, the decision support system may be configured to display a cardiac arrest probability at a moment in time, which may be calculated and/or predicated by the decision support system based on selected criteria. The decision support system may also be configured to track certain criteria in order to suggest treatment outcome probabilities, for example suggesting the treatment pathway with the highest or a high perceived probability of success.

According to some embodiments of the present invention, a monitor, or a defibrillator/monitor combination, or other similar device, may be configured to provide a graphical tool to configure the monitor to follow recognized rescue protocols, for example one or more of the protocols described and/or shown herein. Such a tool may be included on the monitor or defibrillator device, on a tablet or handheld or other computing device, and/or on both, according to embodiments of the present invention. Such a tool may be provided in a graphical interface, for example a flowchart. The tool allows the user to configure the patient monitor to follow a particular rescue protocol, for example by visually presenting a flow chart for the protocol and allowing the user to customize the protocol. For example, the length of the CPR period may be configured by the user to customize the treatment protocol. Such a tool may also permit the downloading and uploading of customized treatment protocols to and/or from a monitoring device, which may also permit the same customized protocol settings to be carried on a mobile device and/or transferred or uploaded to multiple other devices in different locations and/or at different times, according to embodiments of the present invention.

Figure 26:
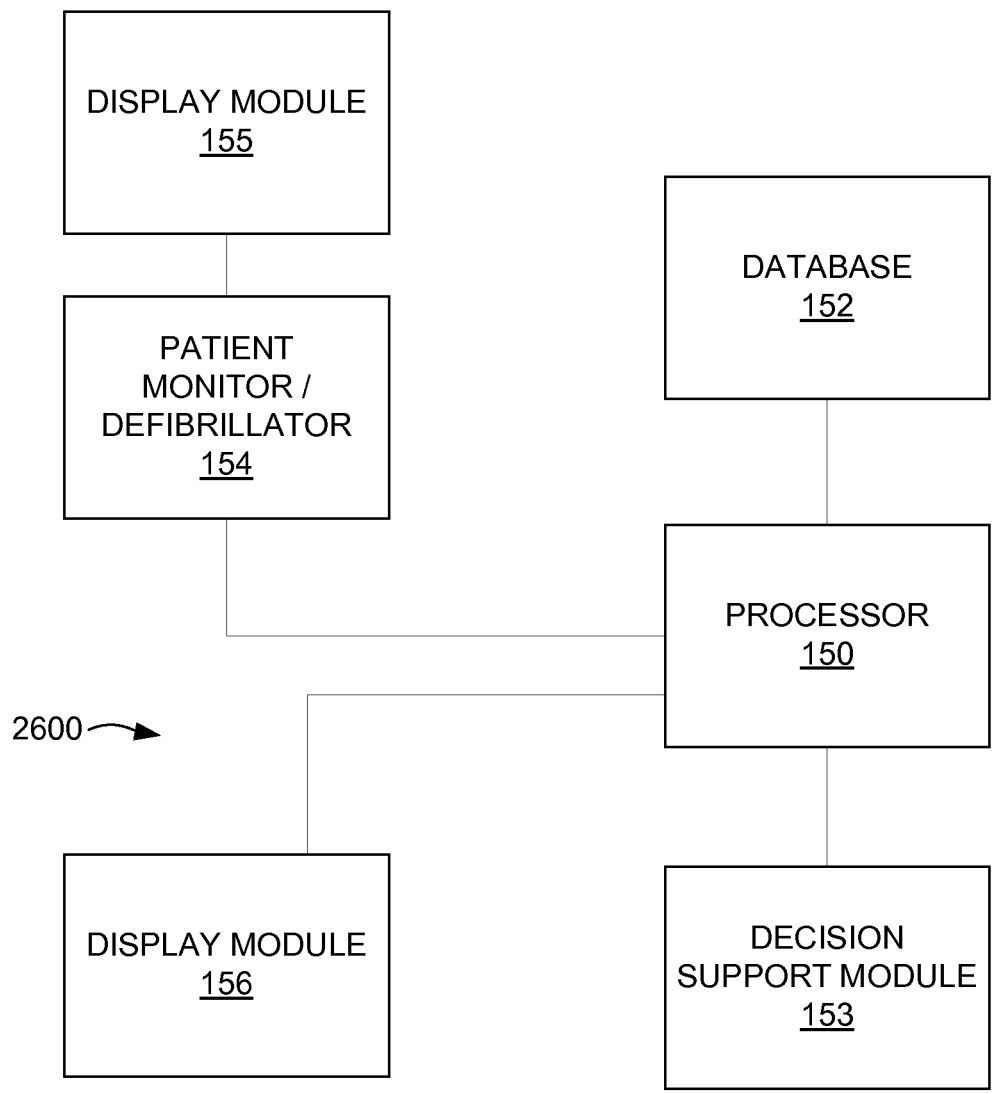
FIG. 26 illustrates a clinical decision support system, according to embodiments of the present invention.

FIG. 26 illustrates a clinical decision support system 2600, according to embodiments of the present invention. System 2600 includes a processor 150 which is communicably coupled to a database 152, a decision support module 153, a display 156, and a patient monitor and/or defibrillator 154, which may itself be communicably coupled to another display module 155, according to embodiments of the present invention. Some or all of the elements shown in FIG. 26 may be part of, or implemented by, one or more computer systems as illustrated in FIG. 27.

Figure 27:
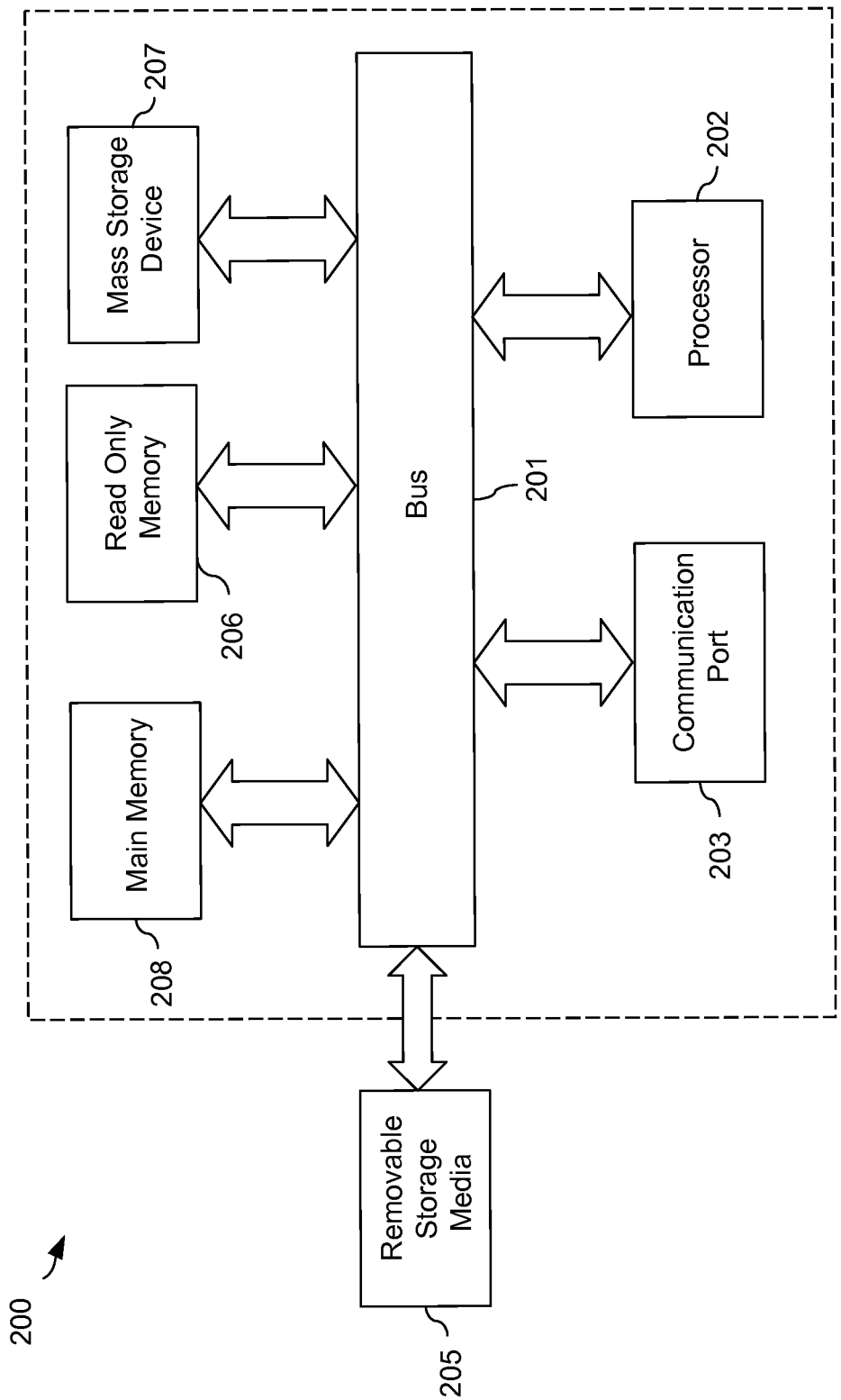
FIG. 27 illustrates a computer system, according to embodiments of the present invention.

FIG. 27 is an example of a computer or computing device system 200 with which embodiments of the present invention may be utilized. For example, defibrillator 154 and/or the tablet shown in FIG. 11 may be or incorporate a computer system 200, according to embodiments of the present invention. According to the present example, the computer system includes a bus 201, at least one processor 202, at least one communication port 203, a main memory 208, a removable storage media 205, a read only memory 206, and a mass storage 207.

Processor(s) 202 can be any known processor, such as, but not limited to, an Intel® Itanium® or Itanium 2® processor(s), or AMD® Opteron® or Athlon MP® processor(s), or Motorola® lines of processors, or any known microprocessor or processor for a mobile device, such as, but not limited to, ARM, Intel Pentium Mobile, Intel Core i5 Mobile, AMD A6 Series, AMD Phenom II Quad Core Mobile, or like devices. Communication port(s) 203 can be any of an RS-232 port for use with a modem based dialup connection, a copper or fiber 10/100/1000 Ethernet port, or a Bluetooth® or WiFi interface, for example. Communication port(s) 203 may be chosen depending on a network such a Local Area Network (LAN), Wide Area Network (WAN), or any network to which the computer system 200 connects. Main memory 208 can be Random Access Memory (RAM), or any other dynamic storage device(s) commonly known to one of ordinary skill in the art. Read only memory 206 can be any static storage device(s) such as Programmable Read Only Memory (PROM) chips for storing static information such as instructions for processor 202, for example.

Mass storage 207 can be used to store information and instructions. For example, flash memory or other storage media may be used, including removable or dedicated memory in a mobile or portable device, according to embodiments of the present invention. As another example, hard disks such as the Adaptec® family of SCSI drives, an optical disc, an array of disks such as RAID (e.g. the Adaptec family of RAID drives), or any other mass storage devices may be used. Bus 201 communicably couples processor(s) 202 with the other memory, storage and communication blocks. Bus 201 can be a PCI/PCI-X or SCSI based system bus depending on the storage devices used, for example. Removable storage media 205 can be any kind of external hard-drives, floppy drives, flash drives, zip drives, compact disc-read only memory (CD-ROM), compact disc-re-writable (CD-RW), or digital video disk-read only memory (DVD-ROM), for example. The components described above are meant to exemplify some types of possibilities. In no way should the aforementioned examples limit the scope of the invention, as they are only exemplary embodiments of computer system 400 and related components.

As shown in FIG. 26, the decision support module 153 may be a clinical support and/or differential diagnosis and/or treatment protocol as described herein. Based on information about the patient received from monitor 154, the decision support module 153 determines and/or shows to the user a set or array of next available options in the decision tree. Alternatively, the decision support module 153 may be configured to calculate probabilities or other statistics based on decision support trees, algorithms, and/or historical data.

Because the display module 155 of the monitor 154 is used for patient-critical monitoring or treatment functions, and because the monitor 154 must often be small or portable, there may be limited size availability on the display device which display module 155 operates. As such, embodiments of the present invention include a separate display 156 which is available to the user or to someone other than the user in order to view information about a particular decision support process being implemented by the processor 150 and, optionally, by the patient monitor 154. When a user decides to implement a decision support process, a selection may be made on the user interface screen operated by the display module 155, and/or may be made on the user interface operated by display module 156. This then prompts the processor 150 to access a clinical decision support process via decision support module 153. Decision support module 153 may include logic to guide the user through the various nodes and/or branches of a clinical decision support process, for example those shown in FIGS. 5-8B and 12-25. According to some embodiments of the present invention, the display module 155 operates the display screen of a monitor/defibrillator as shown in FIG. 11, and the display module 156 operates a tablet computer screen. Such a tablet computing device may be communicably coupled to the processor 150 (whether such processor is located in the monitor/defibrillator or the tablet computing device) by docking it into a communications dock on the monitor/defibrillator as shown in FIG. 11, and/or may be communicably coupled to the processor 150 wirelessly. Based on the disclosure provided herein, one of ordinary skill in the art will recognize that patient monitor 154 may include its own processor, and tasks described as performed by processor 150 may be distributed across one or multiple processors and/or physical devices.

Figure 28:
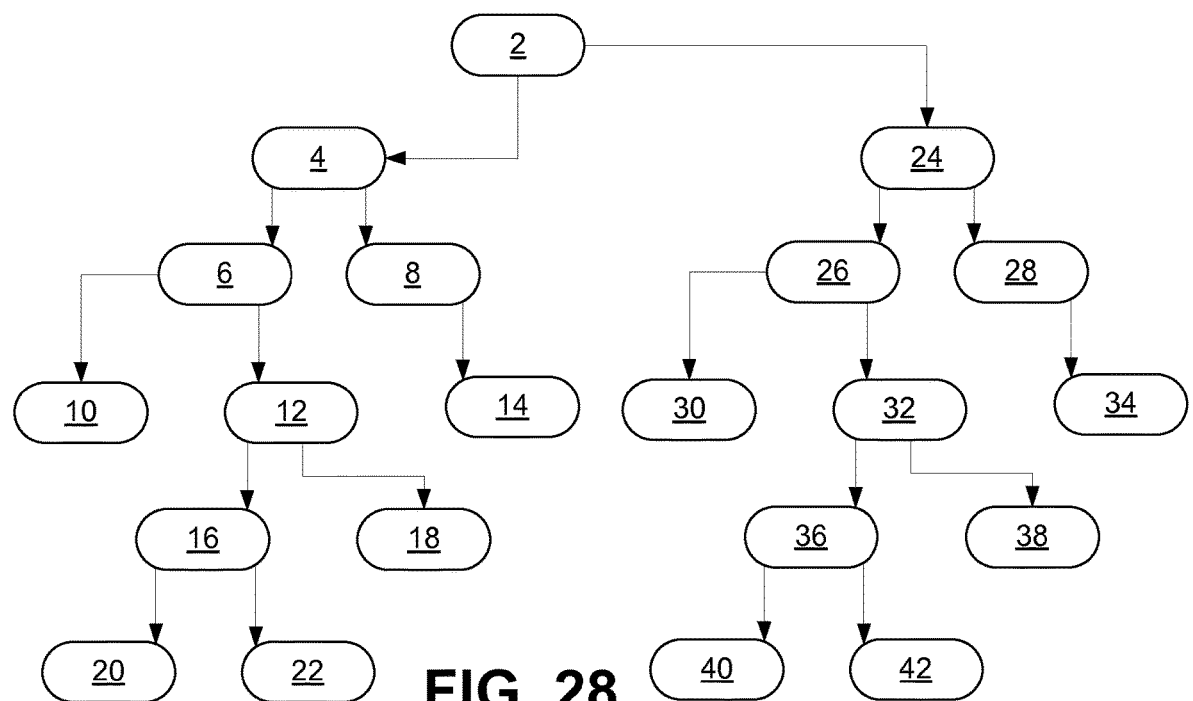
FIG. 28 illustrates a user interface display of a clinical decision support tree, according to embodiments of the present invention.

FIG. 28 illustrates one example of a decision support tree that may be shown to a user on an auxiliary screen (operated by module 156) during a medical event, to guide the user through a treatment protocol or pre-diagnosis of the patient. The decision support module 153 may be navigated through the various decision points (e.g. "nodes") either by manual selection of the next available option or branch, or by complete or partial automatic selection of the next available option or branch based upon patient data collected during the medical event, for example physiological data collected by the patient monitor/defibrillator 154 that is connected to the patient, or by a combination of these two processes. A process that is wholly or partially automatic may also be configured to prompt a user for confirmation before moving to a subsequent or previous node, according to embodiments of the present invention.

Due to the time critical nature of a medical first responder's tasks, such a medical first responder has limited attention resources. In order to further simplify such a user's interface with a decision support module 153, the processor 150 may be configured to dynamically adjust the display screen 156 during the medical event. As one example, FIG. 28 illustrates a user interface display of a clinical decision support tree, according to embodiments of the present invention. This decision support tree begins at block 2, and the first decision is between blocks 4 or 24. If block 4 is selected, the decision is next between blocks 6 and 8. If block 6 is selected, the next decision is between blocks 10 and 12. Although one or two possible branches or decisions are shown, one of ordinary skill in the art will appreciate, based on the disclosure provided herein, that any number of branches or decision options may be provided to extend from a particular node, and that such branches could overlap and/or loop back to a previous node, according to embodiments of the present invention. The remaining blocks 14, 16, 18, 20, 22, 24, 26, 28, 30, 32, 34, 36, 38, 40, and 42 may function in a similar manner.

Figure 29:
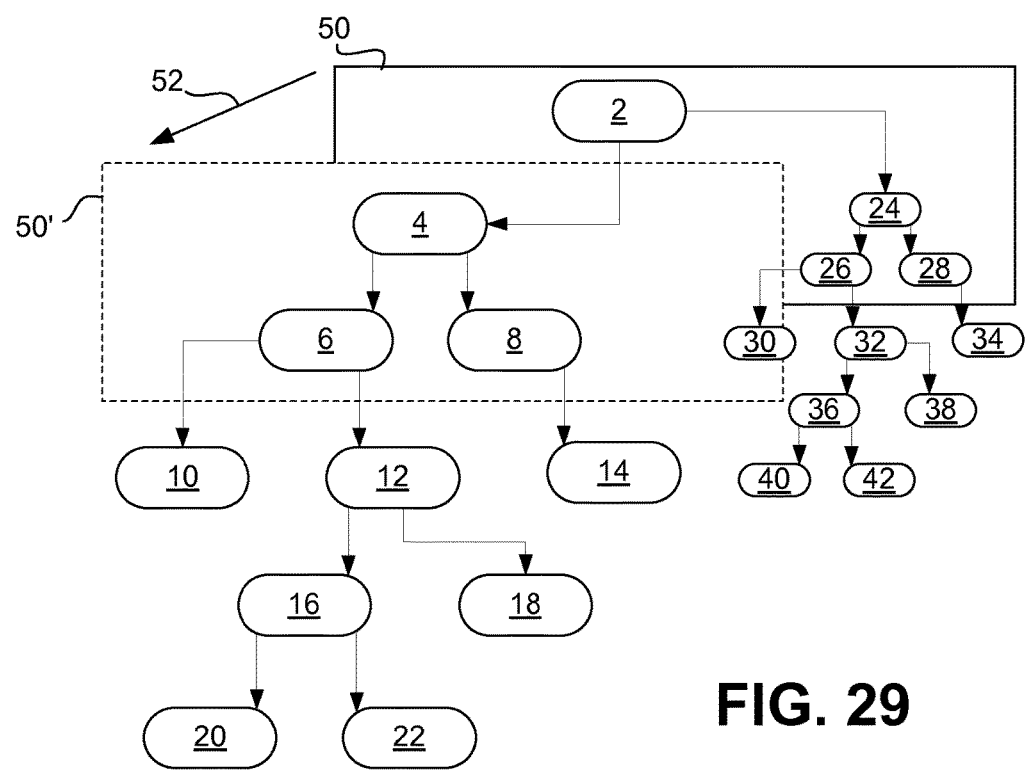
FIG. 29 illustrates the user interface display of FIG. 28 with a portion of the clinical decision support tree resized, according to embodiments of the present invention.

FIG. 29 illustrates one example of the user interface display of FIG. 28 with a portion of the clinical decision support tree resized, according to embodiments of the present invention. Once block 4 is selected over block 24 (manually by the user and/or automatically based on patient data), the display module 156 resizes the entire "branch" including block 24 and its subsequent nodes, and/or resizes each block 24, as shown in FIG. 29, in this case by making them smaller. Alternatively, in another embodiment, even before the user manually selects block 4, the processor 150 instructs the display module 156 to resize the block 24 branch as shown in FIG. 29 based on an indication from the decision support module 153, which factors in patient data received (either manually or automatically from the monitor 154) to indicate that choosing block 4 over block 24 would be more consistent with the particular clinical decision support process being implemented. By indicating a size difference between block 4 and block 24, the user is provided a visual indication which, if it coincides with the user's perceptions and experience, facilitates the navigation through the decision support process. This also makes such a process easier to use for those who may not have extensive experience with a particular decision support protocol.

The resizing may occur by making block 24 smaller, or by making block 4 larger, or both. In some cases, only the subsequent sets of blocks or nodes are resized, rather than the rest of the branches or nodes depending from the immediately subsequent nodes. Each node may be represented by a shape, and the entire border of the shape may be resized in order to indicate a non-chosen or less-probable node. As another alternative, the size of the node may remain the same but the text inside the node may be resized. As yet another alternative, the size of the node may remain the same, but the color or transparency of the non-chosen or less-probable nodes may be changed, for example "grayed out" for the less important nodes and turned to a bolder color or flashing color for the more important nodes. A combination of these and other visual indication features may be employed to assist the user in visually navigating through the decision support process in real time, during the medical event.

Figure 30:
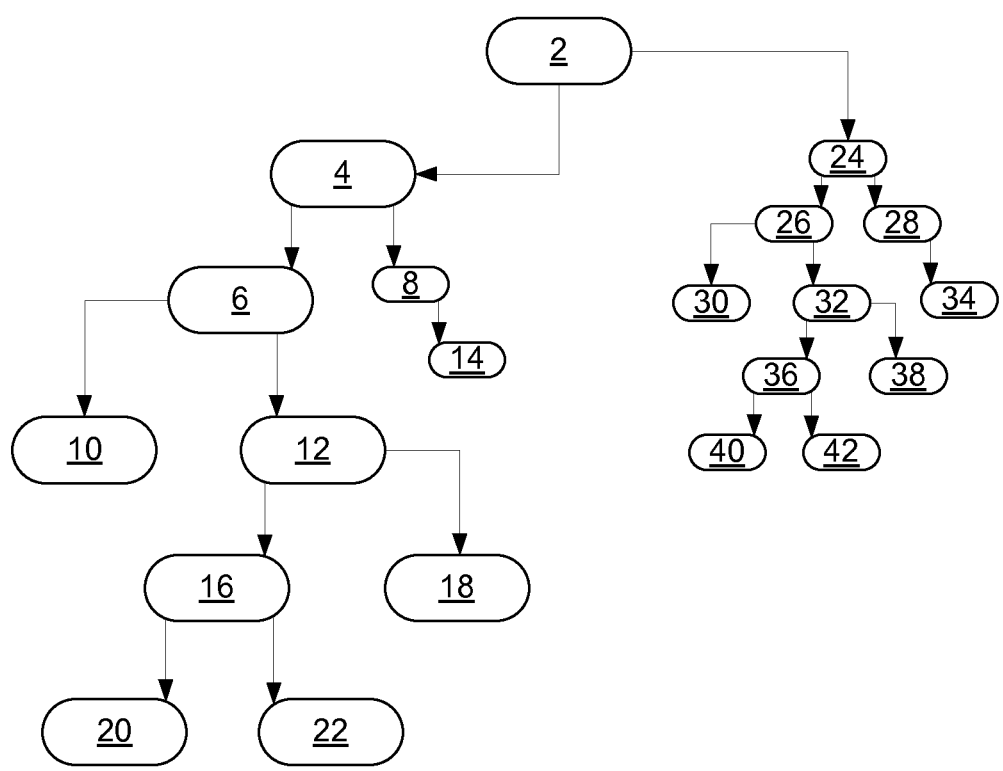
FIG. 30 illustrates the user interface display of FIGS. 28 and 29 with an additional portion of the clinical decision support tree resized, according to embodiments of the present invention.

In some cases, the entire decision support tree may be shown on a device screen; in other cases, the tree may be too large to show all at once. FIG. 29 also illustrates how a screen border can be recentered or moved dynamically to correspond with movement through the tree. For example, screen border 50 is initially centered (either vertically or horizontally or both) on block 2, and as soon as block 4 is selected, or becomes a more likely or recommended selection, the screen border 50 shifts along the direction indicated by arrow 52 to new screen border position 50', which is now centered on block 4. FIG. 30 illustrates a similar resizing feature as it might be displayed after block 6 is selected over block 8.

The decision support module 153 may also be configured to transition between differential diagnosis and treatment protocols; for example, as a likely diagnosis is approached by a clinical support module, the user may be prompted to select or begin a treatment protocol consistent with one or more likely diagnoses or pre-diagnoses. As another example, one or more treatment protocol trees may be presented at the end of a differential diagnosis or clinical decision support tree, in order to guide the user through the recommended treatment protocol once the decision support module 153 has helped the user identify the condition that requires treatment.

The patient monitor/defibrillator device 154 may also be configured for several different care modes, and may be configured to enter the most likely or most relevant care mode based on the user's navigation of the clinical decision support process, for example on auxiliary display 156, and to change between two or more care modes as appropriate as the user navigates the clinical decision support tree, according to embodiments of the present invention.

Figure 31:
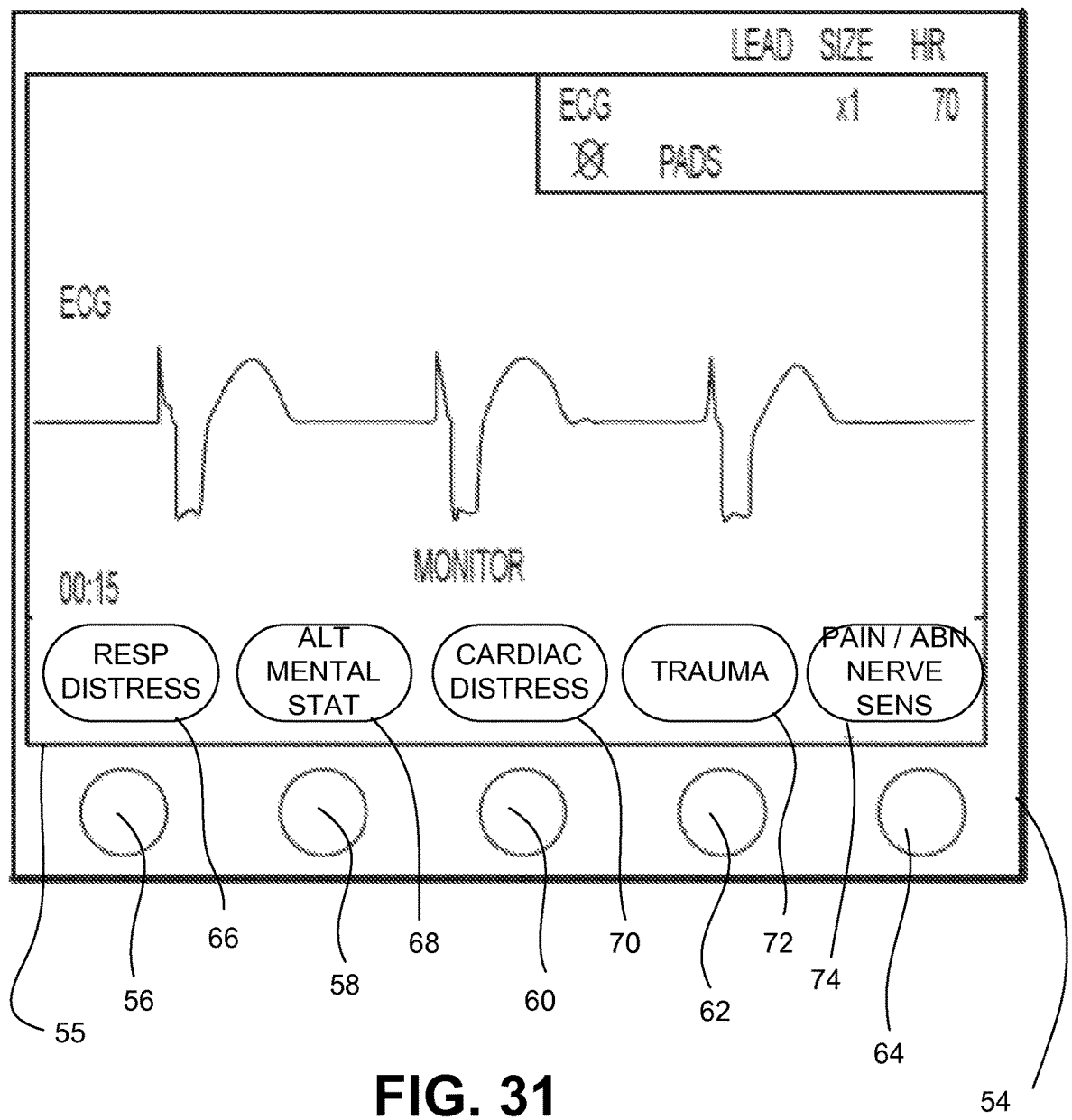
FIG. 31 illustrates a user interface display with dynamic softkeys, according to embodiments of the present invention.

FIG. 31 illustrates a user interface display with dynamic softkeys, according to embodiments of the present invention. Just as the nodes on a decision support tree display may be dynamically visually adjusted to help the user in navigating the process, so too the selection options on a patient monitoring or treatment device 154 may be dynamically adjusted to guide the user through a particular clinical decision support process. FIG. 31 shows a housing of a patient monitor/defibrillator 54, which may include a screen 55 (for example operated by display module 155 of FIG. 26), and which may include a number of physical user input devices 56, 58, 60, 62, 64, which may be for example buttons. The screen 55 may be configured to display a user interface as shown, which may include one or more softkeys 66, 68, 70, 72, 74, with one or more of the softkeys 66-74 corresponding to one or more of the buttons 56-64. Based on the disclosure provided herein, more or fewer buttons and/or softkeys maybe used, and the positioning of the buttons and/or softkeys may vary across different units, models, or designs. For example, the buttons may alternatively or additionally extend vertically across one side of the screen 55.

The softkeys 66 are part of the display screen that may be dynamically modified by the processor 150 and/or the patient monitor 154, such that the buttons 56-64 may be used by the user to select different options at different times. This allows the user to navigate through various menus with a single row of buttons. According to some embodiments of the present invention, the device 55 does not include any physical buttons, and instead uses only softkeys on the display screen 55 that are themselves selectable (e.g. via a touchscreen arrangement). As such, the term "softkey" is used herein in its broadest sense to refer to any combination of physical and virtual buttons that may be used by a user to select from one or more options.

Figure 32:
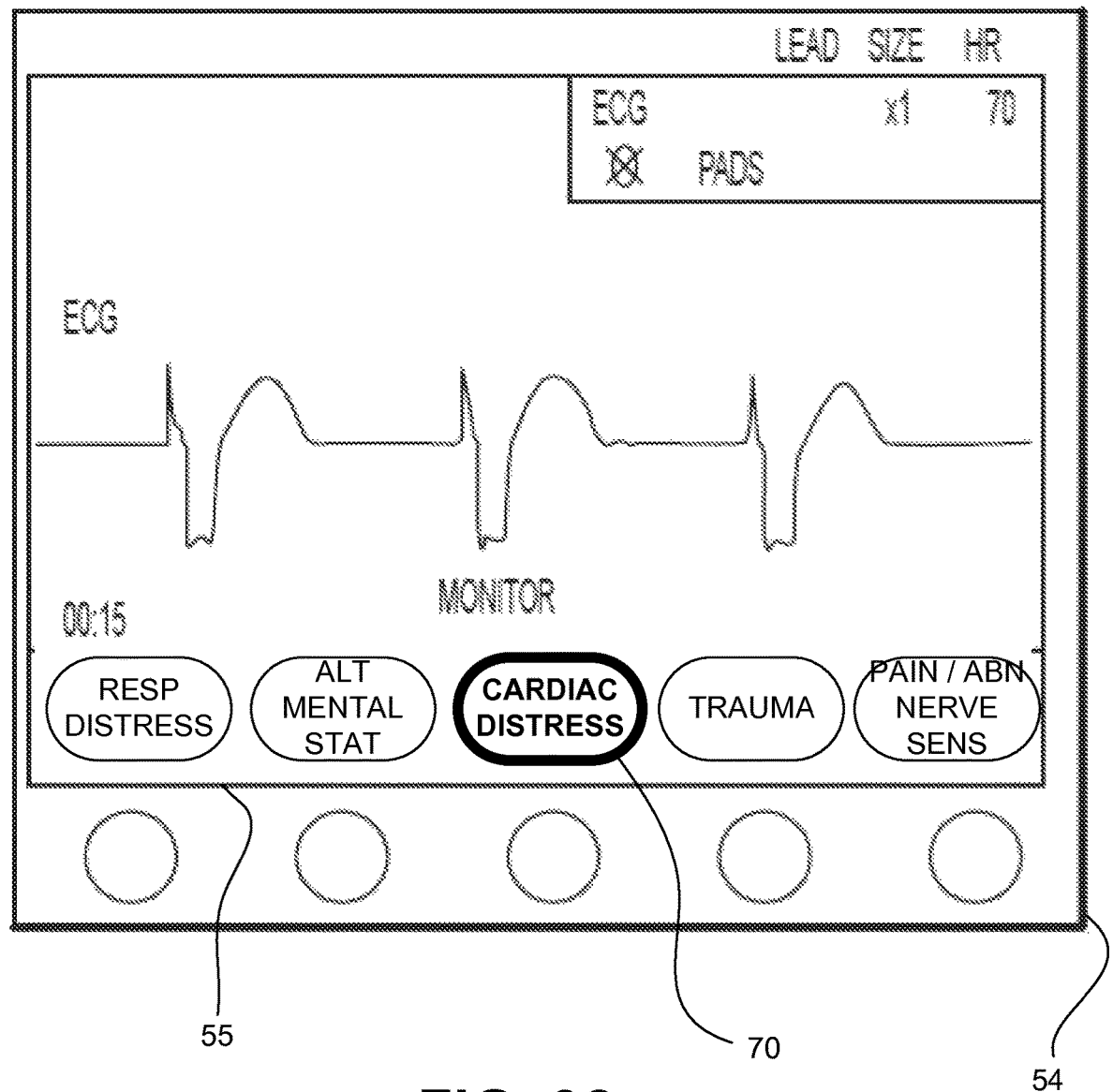
FIG. 32 illustrates the user interface display of FIG. 31 with one softkey emphasized based on clinical decision support, according to embodiments of the present invention.
Figure 33:
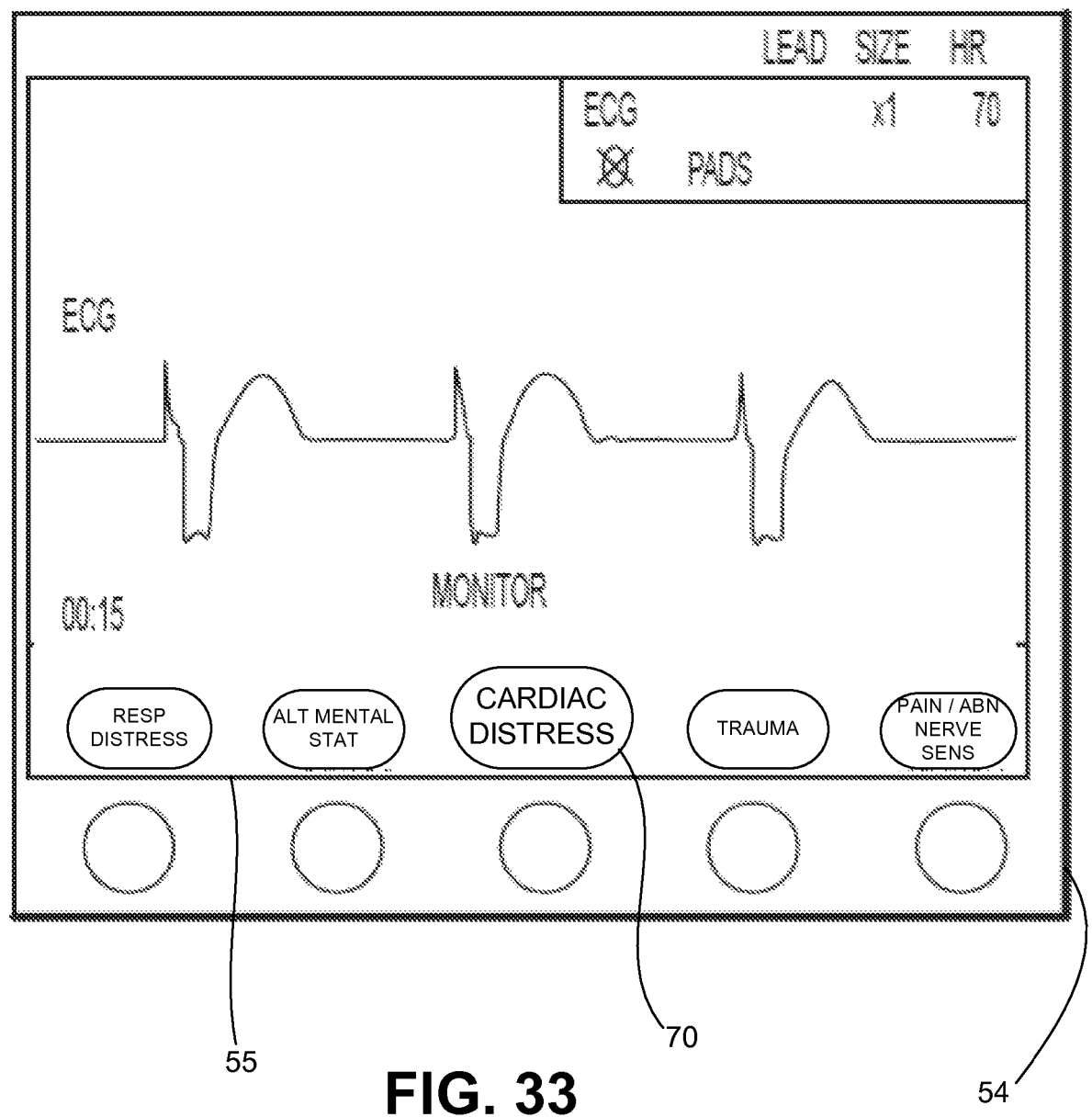
FIG. 33 illustrates the user interface display of FIG. 31 with one softkey emphasized in a different way, based on clinical decision support, according to embodiments of the present invention.

Similar to the process described with respect to FIGS. 28-30, the softkeys 66 may be dynamically adjusted to assist the user in navigating a decision support process. Based on the disclosure provided herein, one of ordinary skill in the art will recognize numerous different menus or clinical decision support processes that may benefit from such dynamically adjusting softkeys. Just a few particular examples are shown in FIGS. 32 and 33. For example, if a user selected the "acute care diagnose" button or softkey from the user interface display of FIG. 3, the user could be taken to the screen of FIG. 31 with dynamic softkeys 66-74. Such softkeys may initially look very similar to those of FIGS. 3 and 31; however, according to one embodiment of the present invention, after the user has entered the acute care diagnosis function, and before the user has selected the next branch of the process, the patient monitor/defibrillator observes a cardiac arrhythmia based on the patient's simultaneously observed ECG waveform. Based on this physiological data, the display module 155 emphasizes the Cardiac Distress softkey 70 by visually emphasizing it or visually distinguishing it over the other simultaneously displayed softkeys, as shown in FIG. 32. For example, the Cardiac Distress softkey 70 may be changed in color or boldness. The softkey 70 may include a displayed geometric shape, and such shape may be changed, or its perimeter may be made bolder or more visually distinct. As another option, the text within the softkey 70 may be enlarged or emboldened or italicized in order to visually distinguish softkey 70 based on the physiological data.

According to some embodiments of the present invention, the user interface displayed on the screen 55, and/or the screen display of an accompanying tablet device, includes one or more legends for visually indicating to the user why one or more softkeys have been emphasized or highlighted. For example, such a legend may include text such as "possible cardiac arrhythmia" to explain why the Cardiac Distress softkey 70 is emphasized, or "low SpO2" to explain why the Respiratory Distress softkey 66 is emphasized, or "dispatch: chief complaint=trauma" to explain why the Trauma softkey 72 is emphasized, according to embodiments of the present invention.

As an alternative, or in combination with the color, font, font size, shape, and similar visual distinguishing features, based on this physiological data, the display module 155 resizes the Cardiac Distress softkey 70 by making it larger, or by making the other softkeys smaller, as shown in FIG. 33. Although FIGS. 32 and 33 illustrate only one softkey 70 being emphasized and/or resized based on available patient data, the display module 155 may further be configured to dynamically emphasize and/or resize more than one softkey, in more than one way, according to embodiments of the present invention. For example, if the patient's blood oxygen content is observed by the monitor 154 as being below a certain threshold, and the patient's ECG waveform is observed by the monitor 154 as being irregular, both the Cardiac Distress softkey 70 and the Respiratory Distress softkey 66 may be visually emphasized or resized with respect to the other softkeys, and may also be visually emphasized or resized with respect to each other depending upon the relative significance of each possible diagnosis or treatment protocol. For example, if the decision support module 153 or processor 150 is able to determine that the cause of the respiratory distress is likely cardiac distress, then the cardiac distress softkey 70 may be the largest or most emphasized softkey, while the respiratory distress softkey 66 may be the next largest or next most emphasized softkey, followed by the remaining softkeys. Once a definitive selection is made, the softkeys 66-74 may be configured to dynamically update to reflect the next decision/step or set of decisions/steps. The dynamic resizing and/or emphasizing of various softkeys conveys a greater level of helpful decision support to the user, without sacrificing the user's ability to select even one of the softkeys that is not enlarged or emphasized, according to embodiments of the present invention.

Although the dynamic adjustment of visual characteristics of softkeys has been described with respect to observed physiological data about the patient, such dynamic adjustment may alternatively or additionally be accomplished using patient charting data or other patient data entered manually or automatically. For example, if the patient's chart at the beginning of the medical event indicates that the patient was involved in an automobile accident, the Trauma softkey 72 may be configured for initial enlargement and/or emphasis as soon as the user selects the "acute care diagnose" function from the interface of FIG. 2, according to embodiments of the present invention.

Figure 34:
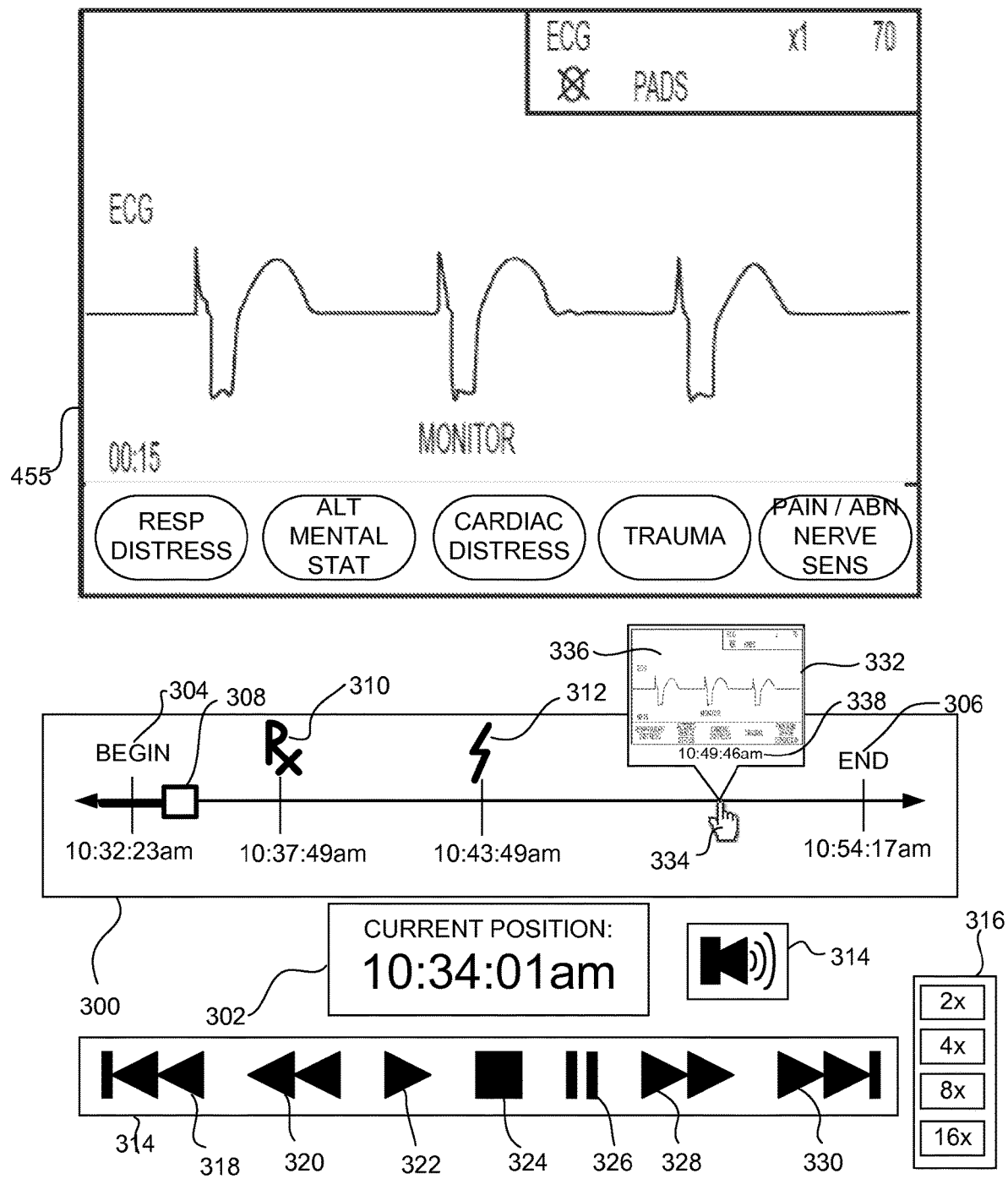
FIG. 34 illustrates a code review interface for reviewing user interface display data corresponding to a medical event, according to embodiments of the present invention.

FIG. 34 illustrates a code review interface for reviewing user interface display data corresponding to a medical event, according to embodiments of the present invention. The code review interface includes a user interface replicator 455 as well as a visual timeline indicator 300. Throughout a medical event, the user of the patient monitor/defibrillator 154 takes the display screen 55 of the monitor 154 through various steps and user interface modes. It is often helpful, after the medical event has occurred, for the user, as well as someone who is reviewing or critiquing the performance of the user, to be able to know what happened during the medical event and when during the medical event such events occurred. Such information is particularly helpful in the time leading up to or following a significant patient event, in order to determine the appropriateness or effectiveness of the particular treatment applied. To this end, the processor 150 may be configured to capture visual representations (e.g. "snapshots" in time) of some or all of the user interface screen 55 and store them for later review, for example in database 152, according to embodiments of the present invention. Such review may be accomplished in the form of a playback interface as shown in FIG. 34. Such snapshots of the user interface 55 may be recorded at least once each second, twice each second, or more times each second, at regular or irregular intervals, according to embodiments of the present invention. In some embodiments, the snapshots may be made frequently enough (e.g. at the data sample rate of 500 snapshots per second) to provide full fidelity playback of the event.

The interface replicator 455 and visual timeline indicator 300 may be configured to play back the screen user interface appearance at the same rate at which the images were taken or captured, and dynamically move the position of the timeline indicator 308 along the timeline 300 from the beginning time indicator 304 to the ending time indicator 306, according to embodiments of the present invention. A current position indicator 302 indicates the time, for example in hour:minute:second format, at which the particular user interface screen shot shown in the user interface replicator 455 was taken (or at which such a user interface displayed during the medical event). As such, a person reviewing the progression of the screen interface 55 sees the screen interface 55 in the user interface replicator 455 just as it would have been seen by the user of the device at the time of the medical event, according to embodiments of the present invention.

The visual timeline indicator 300 may also include visual event indicators, such as drug administration visual event indicator 310 and patient defibrillation visual event indicator 312. Other visual event indicators may include, for example, the occurrence of an alarm, the time at which a blood pressure measurement or signal was acquired (which may be helpful for documenting at the end of a medical event), event markers, clinical decision tree points, the time at which spontaneous circulation returned ("ROSC"), and/or the time at which a "rearrest" softkey was pressed or at which a renewed or subsequent cardiac arrest condition was observed.

Visual event indicator 310 indicates the time during the medical event (e.g. on the timeline) at which a drug was administered to the patient. Visual event indicator 312 indicates the time during the medical event (e.g. on the timeline) at which a defibrillation treatment was applied to the patient, according to embodiments of the present invention. Fewer or more of the same or additional visual event indicators may be used in the visual timeline indicator 300, in order to signal to the reviewer the times at which significant events of interest occurred during the medical event. This then permits the reviewer to skip directly to the user interface time intervals of interest, rather than reviewing all user interface screen shots sequentially, according to embodiments of the present invention. As one example of how a user may skip directly to a desired time for playback of the user interface screen, the user may select timeline indicator 308 with a cursor or other selection process, and drag it left or right on the timeline before releasing it to resume playback at the time corresponding to the new location of the indicator 308, according to embodiments of the present invention. According to some embodiments of the present invention, the user may move the indicator 308 and thus the playback to the time of visual event indicator 310 (or to a time that is a predetermined interval before the time of visual event indicator 310) by simply clicking on visual event indicator 310.

The interface of FIG. 34 may further include a current position indicator 302, which displays a time corresponding to the position of the indicator 308 along the timeline 300 and corresponding to the image displayed in the user interface replicator 455, according to embodiments of the present invention. While FIG. 34 illustrates a substantially linear timeline, other non-linear timeline indicators may be used. The code review interface of FIG. 34 may also be particular helpful in reviewing the recorded screen images for dynamic softkey adjustments, as described with respect to FIGS. 32 and 33. For example, if a user failed to select a particular softkey that was later determined to have been the preferred course of action, the code reviewer could set the indicator 308 to the time that such softkey was displayed to see whether the particular softkey was resized or emphasized in order to indicate that it was the preferred course of action. Reviewers using the interface of FIG. 34 are also able to see what exactly was on the user's screen when certain actions were undertaken, for example what the user looked at just prior to the drug administration event 310, according to embodiments of the present invention. According to some embodiments of the present invention, the interface of FIG. 34 operates in a manner similar to that of digital video recorder playback.

Screen controls consistent with user interfaces that play back movies may be included in the interface of FIG. 34. For example, the interface may include a media navigation interface including media navigation bar 314, volume selection bar 314, and/or playback speed selection bar 316. The media navigation bar 314 may include screen controls similar to those used with playback of movies, to control the content of the user interface replicator. For example, the media navigation bar 314 may include a play button 322, a stop button 324, a pause button 326, a rewind button 320, and a fast forward button 328. A skip back button 314 and skip forward button 330 may also be included, for example to skip between medical events, chapters, and/or visual event indicators, according to embodiments of the present invention. As used herein, "button" is used to refer to either or both of a physical button or a virtual/screen selection interface option. By clicking on or otherwise selecting one of the 2×, 4×, 8×, or 16× portions of the playback speed selection bar 316, the speed at which the medical vent is played on the user interface replicator 455 may be adjusted. The playback speed selection bar 316 may also be configured to visually indicate which of the playback speed selections is currently active. Other or additional speed selections may be provided. Clicking on or otherwise selecting volume selection bar 314 permits adjustment of any audio playback volume (e.g. when audio data from the medical event is also played back simultaneously or instead of the visual data).

According to some embodiments of the present invention, the on-screen cursor 334 (or other selection mechanism) may take the form of a hand with a pointed finger. When the finger is placed over, on, or near the timeline, a display preview pop-up window 332 opens, for example attached or in the vicinity of the finger or cursor 334. The display preview window 332 may show, for example, a physiologic waveform along with static measurements and time and events in sufficient detail for the user to determine whether to select that particular timeline location for current playback, according to embodiments of the present invention. The display preview window 332 includes the physiologic waveform and measurements/events portion 336, as well as a time indicator portion 338 indicating where, along the visual timeline indicator 300, the cursor 334 has been placed, according to embodiments of the present invention. According to some embodiments of the present invention, selecting and "holding" the selection on the timeline indicator 308 and scrolling forward and backward along the timeline 300 causes a similar display preview window 332 to pop up at or near the slider 308.

According to some embodiments of the present invention, the user can play back the clinical decision support tree for reviewing the medical event. For example, a tablet screen, or a screen controlled by display module 156, or alternatively an interface similar to that of FIG. 34, could be configured to indicate a timeline and display the user's progression through a clinical decision support tree by highlighting each node through which the process was taken, and the time at which such node selection was made. According to some embodiments of the present invention, a representation of the clinical decision support tree is itself used as a visual timeline indicator, permitting a user to select a node in order to see, in the user interface replicator 455, what the defibrillator/monitor 154 screen 55 looked like at the time or times when the user was at the selected step in the decision support process. According to some embodiments, the display module 156 and processor 150 may communicably coupled bi-directionally with the defibrillator/monitor 154, and the defibrillator/monitor 154 screen 55 itself may be used as (for example instead of) the user interface replicator 455. In addition to being able to select a particular node in the decision support tree to view the monitor display at that selected step, the tablet computer screen or other display device operated by display module 156 may be configured to show a user-selectable list of event markers which, when selected by the user, replicates the monitor's 154 display at the time of the marked event, either using display module 155 or user interface replicator 455, according to embodiments of the present invention. For example, the following list of event markers could be displayed on a tablet computing device communicably coupled to the defibrillator/monitor 154:

03:05:00 SBP 110/80, HR 99, SpO$_2$ 95%
03:08:00 alarm: SpO$_2$ 88%
03:08:30 event: O$_2$ delivery
03:10:00 SBP 105/82, HR 110, SpO$_2$ 92%
03:11:01 event: ACLS arrive Although FIG. 34 depicts a user interface replicator 455, other replicators may be used to display or play back other observed parameters that occurred over the course of a medical event; for example, graphs, trends, and/or charts representing patient information or physiological status. Such an ability to quickly and efficiently review patient data for a medical event or portions thereof may be helpful not only for a subsequent reviewer, but may also be helpful for the user during the medical event, and/or for a subsequent user during the medical event, for example when a patient is transferred from a Basic Life Support crew to an Advanced Life Support crew. The interface of FIG. 34, or a similar interface, may permit review of the patient's care report, ECG or 12-lead waveforms, cardiopulmonary resuscitation quality, and other patient care information or data. Event markers may be used as described above. As another example, an event marker may be used to indicate that the patient was administered a bronchodilator medication, and the code review interface may be used to look at the patient's respiratory status before and after the application of the bronchodilator. This permits the same user, or a subsequent user for the same patient, or a subsequent reviewer, to observe how effective the bronchodilator dosage was, and perhaps to factor such information into a decision to again administer the same or another treatment. As another example, the interface of FIG. 34 or a similar interface may be used to review how the patient's carbon dioxide waveform changes upon patient treatment. "Snapshots" may be recorded and played back through a similar interface for other patient data, for example the data from a ventilation monitoring device (e.g. minute ventilation).

According to some embodiments of the present invention, alarm thresholds may be dynamically adjusted based on patient physiological data and/or charting data. In addition, frequency-automated measurements, for example blood pressure, may be adjusted based on patient physiological data and/or charting data, for example by changing the frequency of such measurements. For example, when a traumatic brain injury is suspected or diagnosed based on the patient physiological data, charting data, and/or via following a clinical decision support process, the monitor 154 may be configured to automatically obtain vital signs (e.g. blood pressure, SpO$_2$, heart rate, and respiratory rate) every five minutes. For other, less critical conditions, these vital signs may only need to be taken twice during the entire patient event. As another example, automatic blood pressure measurements may be disabled when treating a cardiac patient, and then re-enabled once the patient achieves return of spontaneous circulation.

As another example illustrating how alarm thresholds may be dynamically adjusted based in a traumatic brain injury medical event, a systolic blood pressure ("SBP") alarm may be configured on the monitor 154 to alert the user with an alarm if an adult's SBP is less than 90 mmHg, with a ventilation rate target of 10 breaths per minute, and/or the end tidal carbon dioxide is less than 35 mmHg. These targets may need to be adjusted based on a patient's age; for example, for a three-year old, a systolic blood pressure alarm may be set to activate with an SBP of less than 76 mmHg and/or a ventilation rate target of twenty breaths per minute. For a one-year old, a systolic blood pressure alarm may be set to activate with an SBP of less than 72 mmHg, and/or a ventilation rate target of twenty-five breaths per minute. According to embodiments of the present invention, the processor 150 is configured to automatically adjust the thresholds based on the patient's age, in a traumatic brain injury situation, based on user input, rather than requiring the user to manually reconfigure the alarm thresholds based on age. For example, the processor 150 may obtain the patient's age from database 152, and/or from a patient charting system to which it is communicably coupled, and use the patient's age to automatically reconfigure the alarm thresholds upon an indication, either via a softkey selection or from the decision support module 153, that a traumatic brain injury situation applies. Alternatively, the clinical decision support tree for traumatic brain injury may, at the appropriate node in the process, request the user to select from various age groupings, and use the user's selection from the decision support tree to automatically adjust the alarm thresholds. The processor 150 may also be configured to silence all alarms upon a determination that the patient has entered cardiac arrest, and then re-enable all alarms upon a determination that the patient has achieved a return of spontaneous circulation. According to some embodiments of the present invention, the processor 150 may be configured to, after a cardiac arrest event for an adult, reset the alarm thresholds to end tidal carbon dioxide<30 mmHg (possibly lower for a traumatic brain injury situation) or heart rate<40 beats per minute. While alarm and other thresholds are discussed as being adjustable in traumatic brain injury medical events, alarms and other thresholds may also be dynamically adjusted for other patient events or conditions, according to embodiments of the present invention.

Figure 35:
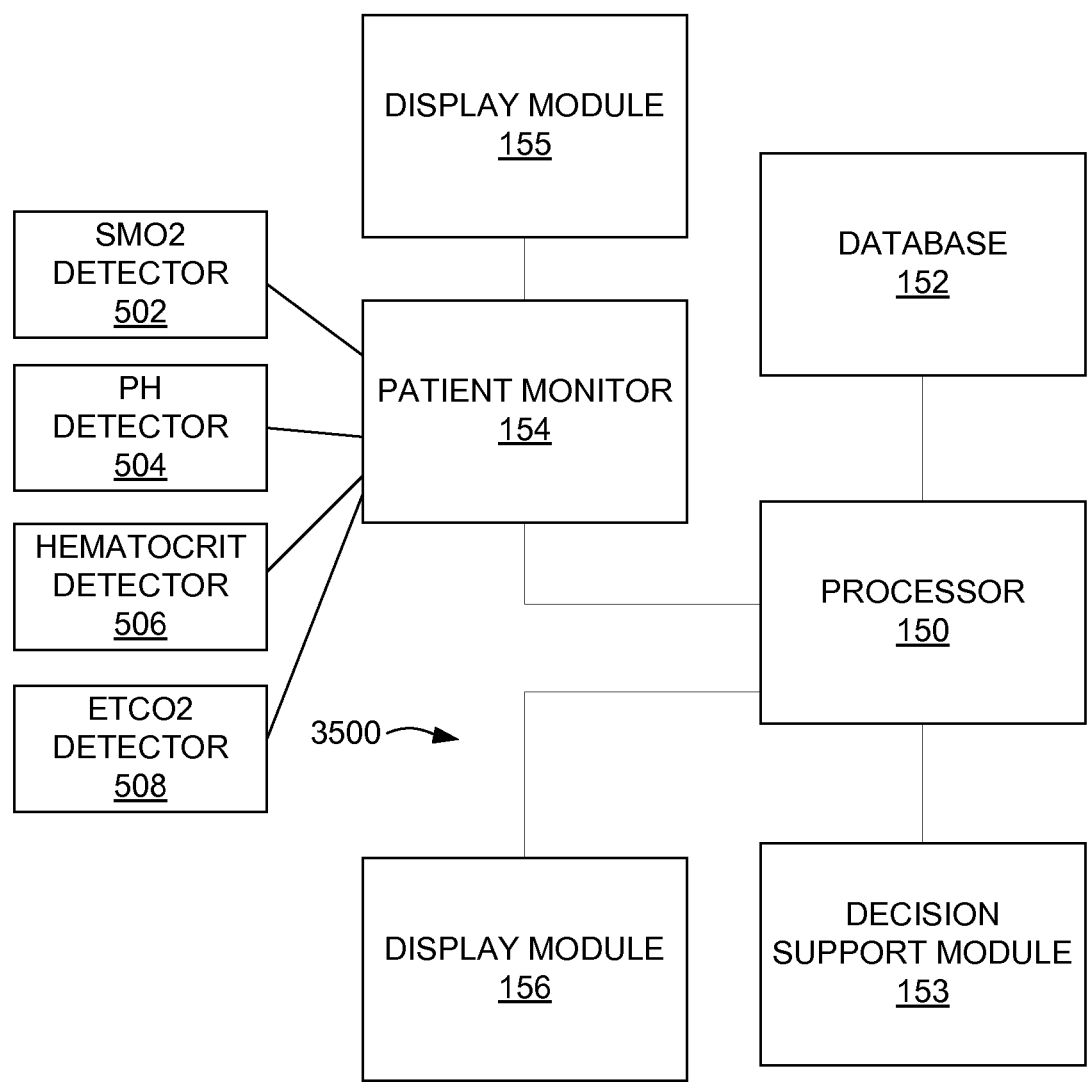
FIG. 35 illustrates a clinical decision support system, according to embodiments of the present invention.

FIG. 35 illustrates a clinical decision support system 3500 similar to that of FIG. 26, with a muscle oxygen saturation detector 502, a pH detector 504, a hematocrit detector 506, and an end tidal carbon dioxide detector 508 in communication with the patient monitoring device 154. Alternatively, detectors 502, 504, 506, 508 may be part of or integral with device 154, according to embodiments of the present invention. In addition to that which is described below, system 3500 operates, or is capable of operating, in the same manner as system 2600, according to embodiments of the present invention. Detectors 502, 504, 506, 508 may be coupled with a patient or otherwise in communication with a patient. Detectors 502, 504, 506, 508 may each be part of a common detector unit which observes infrared spectroscopy characteristics of the patient's blood and applies different algorithms to the same spectroscopy information to calculate and output (to the device 154 and/or processor 150) the muscle oxygen saturation, pH, and/or hematocrit values of the patient. The muscle oxygen saturation detector 502 may be a sensor placed on the patient's muscle, for example on the patient's deltoid, calf, or on the thigh. According to some embodiments of the present invention, the detectors 502, 504, 506, 508 use near infrared spectroscopy to non-invasively determine the respective values of muscle oxygen saturation, pH, and hematocrit. The detectors 502, 504, and/or 506 may each be, or may collectively be, for example a CareGuide™ monitor available from Reflectance Medical, Inc., according to embodiments of the present invention.

Figure 36:
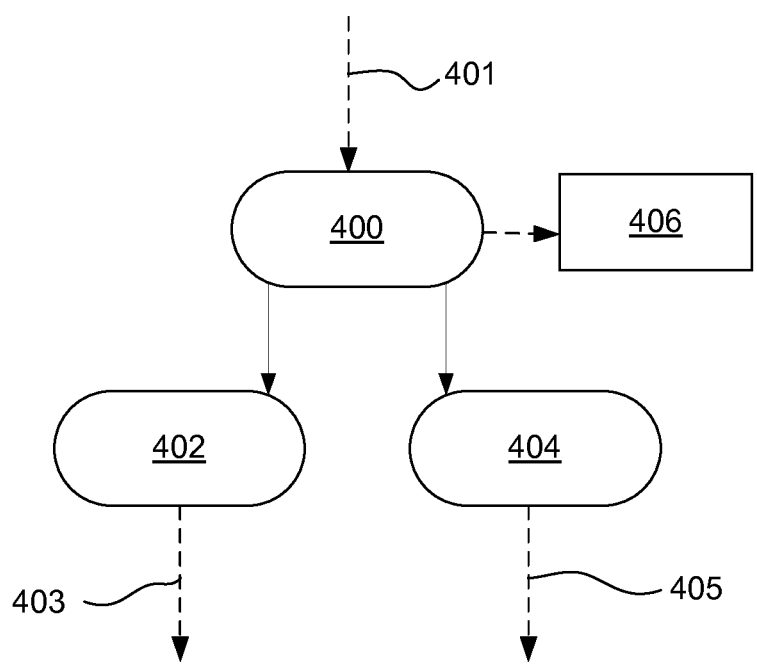
FIG. 36 illustrates a portion of a clinical decision support tree, according to embodiments of the present invention.

One or more of patient muscle oxygen saturation, pH, and hematocrit values may be used by system 3500 in order to assist a user in clinical decision support. Muscle oxygen saturation may be abbreviated as SmO2. For example, as shown in FIG. 36, part of a process, for example a clinical decision support tree, has a decision process that flows through arrow 401 and into decision point 400, system 3500 may assist the decision support module 153 in determining whether to select, suggest, and/or recommend node 402 or node 404, according to embodiments of the present invention. After node 402 is selected, the process may continue to the next node via arrow 403. After node 404 is selected, the process may continue to the next node via arrow 405, according to embodiments of the present invention.

According to one embodiment of the present invention, the portion of the clinical decision support tree of FIG. 36 corresponds to a portion of a decision protocol used for a cardiac arrest patient, which guides the user as to whether, from block 400, the user should perform ventilations along with chest compressions (block 402), or whether the user should perform chest compressions only, with no ventilation (block 404). According to some embodiments of the present invention, in a cardiac arrest patient, muscle oxygen saturation indicates whether a patient needs active ventilation during cardiopulmonary resuscitation. If the muscle oxygen saturation value is too low, for example less than fifty, the clinical decision support system 3500 may, using the decision support module 153, visually indicate node 402 over node 404. If the decision support module 153 determines that the quality of chest compressions is high, and if the patient's muscle oxygen saturation value does not increase during such compressions, the clinical decision support system 3500 may indicate that ventilations should be delivered (node 402), according to embodiments of the present invention. If the muscle oxygen saturation value is within a normal range, for example greater than fifty, or is increasing over the course of delivery of chest compressions, the clinical decision support system 3500 may, using the decision support module 153, visually indicate node 404 over node 402, according to embodiments of the present invention.

According to some embodiments of the present invention, in a cardiac arrest patient, pH indicates whether a patient needs active ventilation during cardiopulmonary resuscitation. If the pH value is too low, for example less than 7.35, or if the pH value is declining during early treatment, the clinical decision support system 3500 may, using the decision support module 153, visually indicate node 402 over node 404. If the pH value is within a normal range, for example at or greater than 7.35, or if the pH value is increasing with treatment, the clinical decision support system 3500 may, using the decision support module 153, visually indicate node 404 over node 402, according to embodiments of the present invention. According to some embodiments of the present invention, a relationship between muscle oxygen saturation and pH indicates whether a patient needs active ventilation during cardiopulmonary resuscitation, in a manner similar to those described above with respect to muscle oxygen saturation and pH individually. The hematocrit value may also be used in a similar manner to indicate whether the blood reaching the patient's muscles has adequate oxygen carrying capacity. In a similar manner, the patient's end tidal carbon dioxide level may be observed by patient monitor 154, and may be used by the decision support module 153 to select between node 402 and node 404. In one embodiment, hematocrit is used to determine the presence of a correctable cause for the cardiac arrest. For example, hematocrit may be increased during a pulmonary embolism. Hematocrit level may be low if the patient has hypoyolemia. Hematocrit may be elevated with a myocardial infarction.

The system's 3500 determination of ventilation needs is not only relevant for deciding whether to actively ventilate a patient when commencing treatment, but also for determining when to commence active ventilation when a patient was not initially ventilated during treatment. Some existing EMS systems do not actively ventilate a patient until six to eight minutes into treatment. Embodiments of the present invention permit the time at which ventilation is initiated to be patient-specific. A patient with a short "down time" and a cardiac etiology often has different ventilation requirements compared to someone with a long "down time" and an arrest of respiratory etiology. Embodiments of the present invention further assist the caregiver in determining not only whether or not to actively ventilate, but also how much to ventilate. If the values of pH and/or SmO2 are low or lowering, or if the value of ETCO2 is high or increasing, the decision support module 153 displays on the display module 155 and/or 156 instructions to increase the frequency or effectiveness of active ventilation, according to embodiments of the present invention.

If adequate oxygen is reaching the patient's muscle tissue, as indicated by the muscle oxygen saturation, tissue CO2, and/or pH values, then ventilations during cardiopulmonary resuscitation may not be needed. Knowing whether or not active ventilations are needed may permit the user, for example a bystander, the EMS technician, or paramedic, to determine whether to initiate or continue ventilations. Applying active ventilation to a patient may require the caregiver to halt chest compressions during the active ventilation. If the patient's muscle tissue is exhibiting a high enough SmO2, and/or a high enough pH, then such caregiver time may be better spent applying chest compressions in some cases. The particular clinical decision support tree being used may include subroutines or tree portions similar to FIG. 36 in looped portions of the tree, or may periodically revisit the portion of FIG. 36, because the SmO2 value and pH value may change over time, during patient treatment, according to embodiments of the present invention.

In addition to helping a caregiver evaluate whether to include active ventilation with chest compressions in treating a cardiac arrest patient, the muscle oxygen saturation and/or pH values may also be used to evaluate the patient's condition over time. By monitoring whether such values improve or deteriorate over time, for example over a period during which cardiopulmonary resuscitation treatment is applied to the patient, feedback can be given to the caregiver to help the caregiver in treating the patient. For example, at block 400, the processor 153, using decision support module 153, determines whether the patient's muscle oxygen saturation and/or pH has improved since the last determination (block 402), or whether the patient's muscle oxygen saturation and/or pH has deteriorated since the last determination (block 404). If the patient's muscle oxygen saturation and/or pH has improved (block 402), the process may continue along a path (arrow 403) toward continued treatment. If the patient's muscle oxygen saturation and/or pH has not improved (block 404), the process may continue along path (arrow 405) to guide the caregiver through additional measures that may be taken to improve these values, and/or may counsel the caregiver regarding whether the patient's muscle oxygen saturation and/or pH indicate that continued cardiopulmonary resuscitation efforts will statistically speaking have little or no chance of reviving or helping the patient. Such information may help the caregiver to determine when to stop treating the patient, according to embodiments of the present invention. In a similar manner, the patient's end tidal carbon dioxide (ETCO2) may be monitored by patient monitor 154 and used by decision support module 153 to, in a similar fashion, determine the efficacy of particular patient treatment over time, and/or to suggest when further treatment is unlikely to revive the patient or affect the patient's outcome. Peripheral oxygen saturation (SpO2) may also indicate ventilation needs; while the SpO2 signal is often poor in cardiac arrest, it may provide relevant information for decision support module 153 if the signal is strong enough. Such information (e.g. involving patient muscle oxygen saturation, end tidal carbon dioxide, and pH level) may also be used as feedback for the compression quality of the chest compressions applied to the patient. The processor 150 may be communicably coupled to a patient treatment device, such as, for example, an AutoPulse® device available from ZOLL Medical®, and configured to provide parameters to the patient treatment device to permit the patient treatment device to automatically change its treatment protocol. For example, if the decision support module 153 determines that the patient's pH, or muscle oxygen saturation, or end tidal carbon dioxide levels are decreasing during cardiopulmonary resuscitation, the processor 150 may instruct the AutoPulse® device, or other automatic chest compression device, to increase the depth and/or frequency of chest compressions. If the patient's muscle oxygen saturation, and/or pH, and/or ETCO2 levels do not change with increasing compression depth and/or compression frequency, this may indicate that the patient will likely have a poor outcome and that termination of resuscitative efforts should be considered. Such an indication may be displayed on display module 156 and/or display module 155, according to embodiments of the present invention.

According to some embodiments of the present invention, the system 3500 may suggest a frequency and/or duration of active ventilation of a patient based on the patient's muscle oxygen saturation and/or pH levels. For example, node 400 of FIG. 36 may lead to additional nodes having different frequencies and/or durations for active ventilation. Alternatively, at node 400 the decision support module 153 may simply generate a suggested or recommended ventilation value 406 based on the patient's muscle oxygen saturation and/or pH levels.

According to some embodiments of the present invention, the patient muscle oxygen saturation and/or pH levels are used to create alarm limits based on thresholds, for example to notify the user (e.g. via display module 156 and/or 155) when the observed values fall outside of the thresholds.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A medical system comprising:
a first sensor configured to:
detect, using near infrared spectroscopy, an initial muscle oxygen saturation (SmO2) level of muscle tissue of a patient who is undergoing cardiac arrest, and
generate a first signal representing the detected initial SmO2 saturation level;
a second sensor configured to provide information for providing feedback on parameters of chest compressions applied to the patient;
a third sensor configured to generate an electrocardiogram (ECG) waveform regarding the patient; and
a user interface device;
a processor communicably coupled to the user interface device, the processor configured to:
cause the user interface device to present a user interface comprising an array of two or more user selectable interface elements concurrently,
wherein a first user selectable interface element of the two or more user selectable interface elements corresponds to a first diagnosis and treatment pathway, wherein the first diagnosis and treatment pathway is associated with a first group of steps for treating respiratory distress, wherein the first user selectable interface element comprises a first label indicating respiratory distress, and
    wherein a second user selectable interface element of the two or more user selectable interface elements corresponds to a second diagnosis and treatment pathway, wherein the second diagnosis and treatment pathway is associated with a second group of steps for treating cardiac arrest, wherein the second user selectable interface element comprises a second label indicating cardiac arrest; and
distinguish, based at least in part on the ECG waveform, between the patient suffering from respiratory distress or the patient suffering from cardiac arrest;
responsive to distinguishing between the patient suffering from respiratory distress or the patient suffering from cardiac arrest, cause the first user selectable interface element or the second user selectable interface element to be emphasized on the user interface;
receive a user selection of the second user selectable interface element;
responsive to receiving the user selection of the second user selectable interface element, cause the user interface device to dynamically update the user interface to include at least some of the second group of steps, wherein causing the user interface device to dynamically update the user interface comprises dynamically updating the first label and the second label to indicate at least some of the second group of steps;
    wherein the second group of steps comprises a first step that indicates a first cardiopulmonary resuscitation (CPR) protocol for treatment of the patient using chest compressions with no ventilation, and
    wherein the second group of steps comprises a second node step that indicates a second CPR protocol for treatment of the patient using chest compressions with active ventilation;
determine whether the parameters of chest compressions are within desired limits;
determine whether the detected initial SmO2 level exceeds a predetermined threshold level;
if the parameters of chest compressions are within desired limits and the detected initial SmO2 level exceeds the predetermined threshold level, emphasize the first step to indicate a suggestion to provide the first CPR protocol for treatment of the patient using chest compressions with no ventilation; and
if the parameters of chest compressions are within desired limits and the detected initial SmO2 level is below the predetermined threshold level, emphasize the second step to indicate a suggestion to provide the second CPR protocol for treatment of the patient using chest compressions with active ventilation.

2. The medical system of claim 1, wherein the processor is further configured to:
receive a pH level of a muscle of the patient, and
determine whether to emphasize the step node or the second step based on at least the detected initial SMO2 level and the pH level.

3. The medical system of claim 1, wherein the processor is further configured to dynamically update the user interface to include at least some of the second group of steps by visually emphasizing the first step or the second step as compared to another step of the second group of step.

4. The medical system of claim 1, wherein the user interface device comprises a user interface display, and the user interface display is a heads up display.

5. The medical system of claim 1, wherein the user interface device comprises a user interface display, and the user interface display is integrated with a hands-free device or wearable device.

6. The medical system of claim 1, wherein the user interface device includes a display projected onto a user's glasses or face shield.

7. The medical system of claim 1, wherein the user interface is a first user interface configured for use by a caregiver of the patient, the medical system further comprising a second user interface device configured for use by a supervisor of the caregiver, and wherein the processor is communicably coupled to the second user interface device, wherein the processor is configured to:
cause the first user interface device and the second user interface device to each present the second group of steps;
if the parameters of chest compressions are within desired limits and the detected initial SmO2 level exceeds the predetermined threshold level, emphasize on both of the first and second user interface devices the first step to indicate the suggestion to provide the first CPR protocol for treatment of the patient using chest compressions with no ventilation; and
if the parameters of chest compressions are within desired limits and the detected initial SmO2 level is below the predetermined threshold level, emphasize on both of the first and second user interface devices the second step to indicate the suggestion to provide the second CPR protocol for treatment of the patient using chest compressions with active ventilation.

8. The medical system of claim 1, wherein the processor is further configured to:
monitor, using near infrared spectroscopy, the SmO2 level of the muscle tissue of the patient who is undergoing cardiac arrest;
determine whether the SmO2 level has increased over the course of delivery of chest compressions;
if the parameters of chest compressions are within desired limits and the SmO2 level has increased over the course of delivery of chest compressions, emphasize the first step to indicate the suggestion to provide the first CPR protocol for treatment of the patient using chest compressions with no ventilation; and
if the parameters of chest compressions are within desired limits and the SmO2 level has not increased over the course of delivery of chest compressions, emphasize the second step to indicate the suggestion to provide the second CPR protocol for treatment of the patient using chest compressions with active ventilation.

9. The medical system of claim 1, further comprising:
a fourth sensor configured to monitor an end tidal carbon diode (ETCO2) level of the patient and to generate a second signal representing the ETCO2 level, and
wherein the processor configured to emphasize, based on the second signal, the first step or the second step to indicate either:
    the suggestion to provide the first CPR protocol for treatment of the patient using chest compressions with no ventilation, or
    the suggestion to provide the second CPR protocol for treatment of the patient using chest compressions with active ventilation.

10. The medical system of claim 1, wherein emphasizing the first step node or the second step comprises:
changing a color of the first step or the second step.

11. The medical system of claim 1, wherein emphasizing the first step or the second step comprises:
increasing a transparency of the second step relative to the first step or the second step.

12. The medical system of claim 1, wherein emphasizing the first step or the second step comprises:
flashing the first step or the second step.

13. The medical system of claim 1, wherein emphasizing the first step or the second step comprises:
increasing a size of the first step or the second step.

14. The medical system of claim 1, wherein the processor further configured to:
determine, based on the first signal, a likelihood of success of reviving the patient, and
cause the user interface device to present the likelihood of success of reviving the patient using the user interface.

15. A method for clinical decision support in a cardiac arrest medical response, the method comprising:
detecting, using near infrared spectroscopy, an initial muscle oxygen saturation (SmO2) level of muscle tissue of a patient who is undergoing cardiac arrest;
generating a signal representing the detected initial SmO2 level;
monitoring parameters of chest compressions applied to the patient;
generating an electrocardiogram (ECG) waveform regarding the patient;
displaying on a user interface device a user interface comprising an array of two or more user selectable interface elements concurrently,
wherein a first user selectable interface element of the two or more user selectable interface elements corresponds to a first diagnosis and treatment pathway, wherein the first diagnosis and treatment pathway is associated with a first group of step for treating respiratory distress, wherein the first user selectable interface element comprises a first label indicating respiratory distress, and
wherein a second user selectable interface element of the two or more user selectable interface elements corresponds to a second diagnosis and treatment pathway, wherein the second diagnosis and treatment pathway is associated with a second group of step for treating cardiac arrest, wherein the second user selectable interface element comprises a second label indicating cardiac arrest;
distinguishing, based at least in part on the ECG waveform, between the patient suffering from respiratory distress or the patient suffering from cardiac arrest;
responsive to distinguishing between the patient suffering from respiratory distress or the patient suffering from cardiac arrest, causing the first user selectable interface element or the second user selectable interface element to be emphasized on the user interface;
receiving a user selection of the second user selectable interface element;
responsive to receiving the user selection of the second user selectable interface element, dynamically updating the user interface on the user interface device to include at least some of the second group of steps, wherein causing the user interface device to dynamically update the user interface comprises dynamically updating the first label and the second label to indicate at least some of the second group of steps;
wherein the second group of steps comprises a first step that indicates a first cardiopulmonary resuscitation (CPR) protocol for treatment of the patient using chest compressions with no ventilation, and
wherein the second group of steps comprises a second step that indicates a second CPR protocol for treatment of the patient using chest compressions with active ventilation;
determining whether the parameters of chest compressions are within desired limits;
determining whether the detected initial SmO2 level exceeds a predetermined threshold level;
if the parameters of chest compressions are within desired limits and the detected initial SmO2 level exceeds the predetermined threshold level, emphasizing the first step to indicate a suggestion to provide the first CPR protocol for treatment of the patient using chest compressions with no ventilation; and
if the parameters of chest compressions are within desired limits and the detected initial SmO2 level is below the predetermined threshold level, emphasizing the second step to indicate a suggestion to provide the second CPR protocol for treatment of the patient using chest compressions with active ventilation.

16. The method of claim 15, further comprising:
monitoring a pH level of a muscle of the patient,
wherein the determination of whether to emphasize the first step or the second step is based on at least the detected initial SMO2 level and the pH level.

17. The method of claim 15, wherein dynamically updating the user interface on the user interface to include at least some of the second group of steps comprises visually emphasizing the first step or the second step as compared to another step of the second group of steps.

18. The method of claim 15, wherein the user interface device comprises a user interface display, and the user interface display is a heads up display.

19. The method of claim 15, wherein the user interface device comprises a user interface display, and the user interface display is integrated with a hands-free device or wearable device.

20. The method of claim 15, wherein the user interface device includes a display projected onto a user's glasses or face shield.

21. The method of claim 15, wherein the user interface device is a first user interface device, the method further comprising:
displaying on the first user interface device and a second user interface device the second group of steps;
if the parameters of chest compressions are within desired limits and the detected initial SmO2 level exceeds the predetermined threshold level, emphasizing the first step on both of the first and second user interface devices to indicate the suggestion to provide the first CPR protocol for treatment of the patient using chest compressions with no ventilation; and
if the parameters of chest compressions are within desired limits and the detected initial SmO2 level exceeds the predetermined threshold level, emphasizing the second step on both of the first and second user interface devices to indicate the suggestion to provide the second CPR protocol for treatment of the patent using active chest compressions with active ventilation.

22. The method of claim 15, further comprising:
monitoring, using near infrared spectroscopy, the SmO2 level of the muscle tissue of the patient who is undergoing cardiac arrest;

determining whether the SmO2 level has increased over the course of delivery of chest compressions;

if the parameters of chest compressions are within desired limits and the SmO2 level has increased over the course of delivery of chest compressions, emphasize the first step to indicate the suggestion to provide the first CPR protocol for treatment of the patient using chest compressions with no ventilation; and if the parameters of chest compressions are within desired limits and the SmO2 level has not increased over the course of delivery of chest compressions, emphasize the second step to indicate the suggestion to provide the second CPR protocol for treatment of the patient using chest compressions with active ventilation.

* * * * *

UNITED STATES PATENT AND TRADEMARK OFFICE
CERTIFICATE OF CORRECTION

PATENT NO. : 11,622,726 B2
APPLICATION NO. : 14/227785
DATED : April 11, 2023
INVENTOR(S) : Gary A. Freeman and Annemarie Elizabeth Silver It is certified that error appears in the above-identified patent and that said Letters Patent is hereby corrected as shown below:

In the Claims

Column 29, Line 38, Claim 1, after "second", delete "node"

Column 29, Line 60, Claim 2, before "step", insert -- first --

Column 29, Line 60, Claim 2, after "step", delete "node"

Column 30, Line 57, Claim 9, delete "diode" and insert -- dioxide --

Column 31, Line 2, Claim 10, after "step", delete "node'"

Column 32, Line 62, Claim 21, delete "patent" and insert -- patient --

Signed and Sealed this
Thirtieth Day of May, 2023

Katherine Kelly Vidal
*Director of the United States Patent and Trademark Office*